(12) United States Patent
Shekhar et al.

(10) Patent No.: US 8,207,992 B2
(45) Date of Patent: Jun. 26, 2012

(54) COMPOSITE IMAGES FOR MEDICAL PROCEDURES

(75) Inventors: Raj Shekhar, Elkridge, MD (US); Omkar Dandekar, Hillsboro, OR (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 12/746,513

(22) PCT Filed: Dec. 5, 2008

(86) PCT No.: PCT/US2008/085705
§ 371 (c)(1),
(2), (4) Date: Feb. 4, 2011

(87) PCT Pub. No.: WO2009/076218
PCT Pub. Date: Jun. 18, 2009

(65) Prior Publication Data
US 2011/0262016 A1 Oct. 27, 2011

Related U.S. Application Data

(60) Provisional application No. 61/012,242, filed on Dec. 7, 2007.

(51) Int. Cl.
*G09G 5/00* (2006.01)
(52) U.S. Cl. ........................ 345/648; 382/128; 382/294
(58) Field of Classification Search .................. 382/128
See application file for complete search history.

(56) References Cited

U.S. PATENT DOCUMENTS

| | | | | |
|---|---|---|---|---|
| 5,633,951 A | * | 5/1997 | Moshfeghi | 382/154 |
| 5,956,418 A | * | 9/1999 | Aiger et al. | 382/154 |
| 6,670,614 B1 | * | 12/2003 | Plut et al. | 250/363.04 |
| 6,775,405 B1 | * | 8/2004 | Zhu | 382/154 |
| 7,206,462 B1 | * | 4/2007 | Betke et al. | 382/280 |
| 7,280,710 B1 | * | 10/2007 | Castro-Pareja et al. | 382/303 |

(Continued)

OTHER PUBLICATIONS

R. Shekhar and V. Zagrodsky, Mutual Information-based rigid and nonrigid registration of ultrasound volumes, IEEE Transactions in Medical Imaging, Jan. 1, 2002, pp. 9-22, vol. 21, No. 1, Publisher: IEEE, Published in: New York, NY USA.*

(Continued)

*Primary Examiner* — Sath V Perungavoor
(74) *Attorney, Agent, or Firm* — Evans & Molinelli PLLC; Eugene J. Molinelli

(57) ABSTRACT

Medical imaging often involves the collective use of information presented in multiple images of an individual, such as images generated through different imaging modalities (X-ray, CT, PET, etc.) The use of a composite of these images may involve image registration to adjust for the variable position and orientation discrepancies of the individual during imaging. However, registration may be complicated by soft tissue deformation between images, and implementations (particularly pure software implementations) of the mathematical models used in image registration may be computationally complex and may require up to several hours. Hardware architectures are presented that apply the mathematical techniques in an accelerated manner, thereby providing near-realtime image registration that may be of particular use for the short timeframe requirements of surgical environments. The composite image generated thereby may be used to target anatomic features of interest during various medical procedures, including surgical procedures. Moreover, such techniques may be applied to computationally difficult image processing techniques, such as the display of a composite image based at least in part on a PET image, which may otherwise be difficult to utilize in a time-sensitive manner such as a surgical setting.

14 Claims, 13 Drawing Sheets

U.S. PATENT DOCUMENTS

| | | | |
|---|---|---|---|
| 7,372,984 B2* | 5/2008 | Dickinson et al. | 382/131 |
| 7,483,034 B2* | 1/2009 | Chefd'hotel et al. | 345/582 |
| 7,639,896 B2* | 12/2009 | Sun et al. | 382/294 |
| 7,689,021 B2* | 3/2010 | Shekhar et al. | 382/131 |
| 7,715,654 B2* | 5/2010 | Chefd'hotel et al. | 382/294 |
| 7,822,291 B2* | 10/2010 | Guetter et al. | 382/294 |
| 7,840,249 B2* | 11/2010 | Wang et al. | 600/407 |
| 7,876,938 B2* | 1/2011 | Huang et al. | 382/128 |
| 7,948,503 B2* | 5/2011 | Shekhar et al. | 345/648 |
| 8,031,211 B2* | 10/2011 | Shekhar et al. | 345/648 |
| 2005/0089213 A1* | 4/2005 | Geng | 382/154 |
| 2005/0190189 A1* | 9/2005 | Chefd'hotel et al. | 345/501 |
| 2006/0029291 A1* | 2/2006 | Sun et al. | 382/294 |
| 2006/0093209 A1* | 5/2006 | Guetter et al. | 382/159 |
| 2006/0247513 A1* | 11/2006 | Wang et al. | 600/410 |
| 2006/0275745 A1* | 12/2006 | Schwarz | 435/4 |
| 2007/0081712 A1* | 4/2007 | Huang et al. | 382/128 |
| 2008/0265166 A1* | 10/2008 | Shekhar et al. | 250/363.03 |
| 2008/0317317 A1* | 12/2008 | Shekhar et al. | 382/131 |
| 2009/0116716 A1* | 5/2009 | Zhou | 382/131 |
| 2010/0027861 A1* | 2/2010 | Shekhar et al. | 382/131 |
| 2011/0052033 A1* | 3/2011 | Shekhar et al. | 382/131 |
| 2011/0193882 A1* | 8/2011 | Shekhar et al. | 345/648 |
| 2011/0262016 A1* | 10/2011 | Shekhar et al. | 382/131 |
| 2011/0311118 A1* | 12/2011 | Shekhar et al. | 382/128 |

OTHER PUBLICATIONS

V. Walimbe, V. Zagrodsky, S. Raja, B. Bybel, M. Kanvinde and R. Shekhar, Elastic registration of three-dimensional whole body CT and PET images by quaternion-based interpolation of multiple pie, Medical Imaging 2004: Image Processing, Jan. 1, 2004, pp. 119-128, vol. SPI EProceedings 5370, No. 1605-7422/04, Publisher: SPIE.*
International Search Report and Written Opinion, PCT/US2008/085705, Jun. 18, 2009, pp. 1-4.

* cited by examiner

160

| Pass | Subdivisions in Voxel Sets | Voxels per Subdivision | Mutual Information Calculation Time (Per Voxel) | | Speedup |
|---|---|---|---|---|---|
| | | | Software Implementation | FPGA Implementation | |
| 1 | 1x1x1 | 256x256x256 | 9,410 ms | 225.42 ms | 41.74 |
| 2 | 2x2x2 | 128x128x128 | 1,209 ms | 30.19 ms | 40.05 |
| 3 | 4x4x4 | 64x64x64 | 166 ms | 4.16 ms | 39.9 |
| 4 | 8x8x8 | 32x32x32 | 18 ms | 0.78 ms | 23.08 |
| 5 | 16x16x16 | 16x16x16 | 10 ms | 0.46 ms | 21.74 |

| Data Set | Total Execution Time | | Speedup |
|---|---|---|---|
| | Software Implementation | FPGA Implementation | |
| iCT to preCT | 11,520 s | 371 s | 31.05 |
| iCT to PET | 11,146 s | 339 s | 32.88 |

FIG. 9B

COMPOSITE IMAGES FOR MEDICAL PROCEDURES

CROSS REFERENCE TO RELATED APPLICATION(S)

The present application is a national phase application of PCT Application No. PCT/US2008/085705, filed on Dec. 5, 2008, and claims priority to U.S. Provisional Patent Application No. 61/012,242, filed on Dec. 7, 2007, the entireties of which are hereby incorporated by reference herein.

STATEMENT REGARDING FEDERALLY FUNDED RESEARCH

This invention was made with government support under federal grant nos. DAMD17-03-2-0001 and DAMD17-99-1-9034, awarded by the U.S. Department of Defense (TATRC). The government has certain rights in the invention.

BACKGROUND

Contemporary medical and surgical techniques, including minimally invasive surgical techniques, frequently involve the imaging of a body or portion thereof of an individual with multiple imaging modalities, such as X-ray, X-ray computed tomography (CT), magnetic resonance imaging (MRI), ultrasound, and positron emission tomography (PET). Each imaging modality provides a distinct set of information; for example, X-ray imaging may provide more information about bony structures, whereas X-ray computed tomography (CT) imaging may provide more information about soft tissues, and positron emission tomography (PET) imaging may provide more information about the location and concentration of a radiolabeled substance. Images from multiple imaging modalities may be collected at various times and by various systems, and the information provided therein may be useful to healthcare providers for diagnosis and treatment, such as the identification, classification, localization, and interventional targeting of tumors and other tissue abnormalities.

SUMMARY

The following presents a simplified summary of the disclosure in order to provide a basic understanding of some aspects of the disclosure. This summary is not an extensive overview of the disclosure. It is intended neither to identify key or critical elements of the disclosure nor to delineate the scope of the disclosure. Rather, its primary purpose is merely to present one or more concepts of the disclosure in a simplified form as a prelude to the more detailed description that is presented later.

In the field of medical imaging, the use of information provided via multiple images (such as images generated from different modalities) may be problematic due to the difficulty in aligning corresponding anatomic structures. Healthcare providers typically generate multiple images from multiple imaging modalities, evaluate each image in turn, and attempt to synthesize diagnostic, prognostic, and/or therapeutic information based on the individual evaluation of each image.

An alternative that may be advantageous involves combining images generated from multiple imaging modalities to produce a composite image illustrating the anatomic structures as evaluated by multiple modalities. Many forms of combination may be possible, such as an additive overlay (illustrating an overlap of features illustrated in each image) and a subtractive overlay (illustrating a change in imaged anatomy over time, e.g., changes to a tumor apparent in several images taken over time.)

However, the generation of a composite image may be difficult to achieve in light of the imperfect mismatch between the images. Because the various images may be taken at different times and with the individual in different positions, the imaged tissue may be differently positioned, oriented, twisted, etc., and the anatomic features illustrated therein may be difficult to align in order to localize and target a desired portion of the body. Moreover, the soft tissues may be deformed (compressed, stretched, pressured, twisted, etc.) between one image and another, and the alignment of anatomic reference points in the various images may be inadequate to reconcile the soft tissue deformities.

Some mathematical models have been devised for registering medical images that account for the deformable characteristics of soft tissues. These mathematical models are capable of registering medical images while accounting for the elastic deformation of soft tissue structures in one image with respect to the other. However, the mathematical techniques presented therein are computationally difficult, such that many image registration embodiments thereof are not capable of providing images on a near-realtime basis. For example, in one software implementation, registering two images using an ordinary software implementation of the techniques presented therein may require as much as 3.2 hours. If the computation is to be performed during a medical or surgical procedure—e.g., where one of the images is intraoperatively generated—then the software implementation may be inadequately responsive to satisfy the needs of the medical practitioners.

Alternatively, implementations may be devised that accelerate certain portions of these techniques, such as by incorporating specialized hardware that performs part or all of the disclosed techniques. Techniques for combining such images, including methods and systems configured for performing such techniques with near-realtime performance, may be devised to produce a composite medical image that illustrates various anatomic structures based on analysis via multiple imaging modalities. The composite images generated thereby may then be used to provide diagnostic, prognostic, and/or therapeutic health information that a healthcare provider may utilize while performing various medical services.

Accordingly, some architectures are discussed herein that may implement these nonrigid tissue modeling techniques with improved responsiveness, and which may be used to produce a composite medical image that may be used to inform a medical procedure. For example, one architecture presented herein may be capable of registering two images in a period of 6 minutes, thereby providing an acceptably responsive image registration that medical practitioners may be able to use in near-realtime, such as in a surgical setting where one of the images is intraoperatively generated. Some variations on these architectures will also be discussed that may present additional advantages and/or reduce or resolve problems that may occur in other implementations.

To the accomplishment of the foregoing and related ends, the following description and annexed drawings set forth in detail certain illustrative aspects and implementations of the disclosure. These are indicative of but a few of the various ways in which one or more aspects of the present disclosure may be employed. Other aspects, advantages, and novel features of the disclosure will become apparent from the following detailed description of the disclosure when considered in conjunction with the annexed drawings.

BRIEF DESCRIPTION OF THE DRAWINGS

FIG. 9A is a table of performance metrics of various implementations of the techniques discussed herein.

FIG. 9B is another table of performance metrics of various implementations of the techniques discussed herein.

DETAILED DESCRIPTION

Figure 1A:
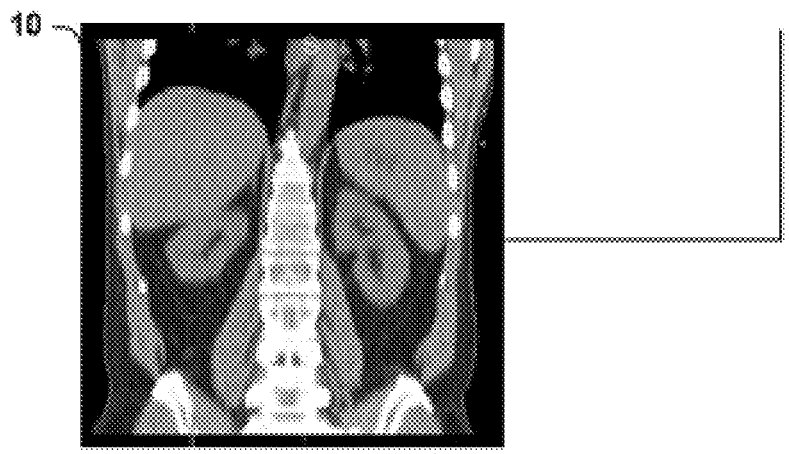
FIG. 1A is an X-ray computed tomography (CT) coronal plane cross-section image of an abdomen of another individual.

One or more aspects of the present disclosure are described with reference to the drawings, wherein like reference numerals are generally utilized to refer to like elements throughout, and wherein the various structures are not necessarily drawn to scale. In the following description, for purposes of explanation, numerous specific details are set forth in order to provide a thorough understanding of one or more aspects of the present disclosure. It may be evident, however, to one skilled in the art that one or more aspects of the present disclosure may be practiced with a lesser degree of these specific details. In other instances, well-known structures and devices are shown in block diagram form in order to facilitate describing one or more aspects of the present disclosure.

As discussed herein, medical practitioners may rely on information collectively presented in a plurality of medical images (e.g., images from different modalities) of an individual's body for the purposes of medical and surgical assessment and treatment. The information from images captured according to multiple modalities may be advantageously combined to produce a composite medical image, which may be used to inform medical procedures. These medical images are combined into a composite medical image by registering the images with respect to each other in order to present information for the same tissues, such as by aligning anatomic reference points.

Figure 1B:
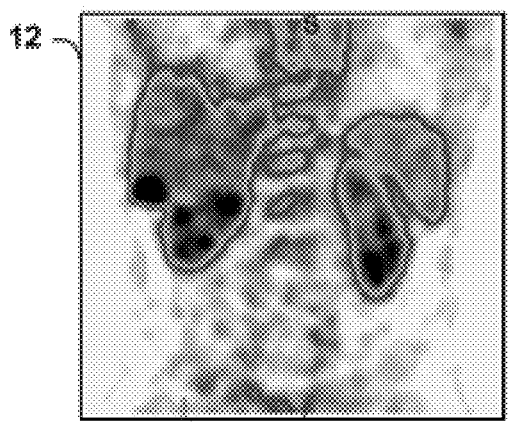
FIG. 1B is a positron emission tomography (PET) coronal plane cross-section image of the abdomen of the individual illustrated in FIG. 1A.
Figure 1C:
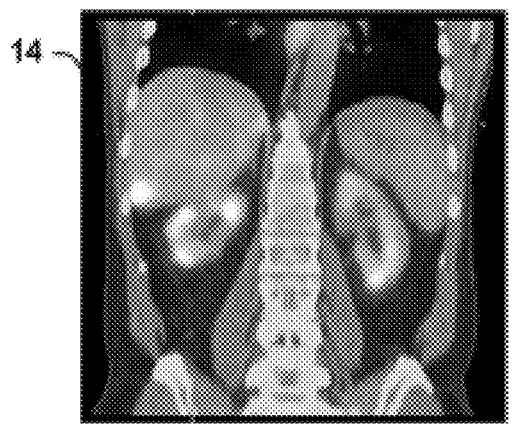
FIG. 1C is a composite coronal plane cross-section image of the abdomen generated from the CT image of FIG. 1A and the PET image of FIG. 1B.

The advantages of such a composite image are illustrated in FIGS. 1A-1C, which illustrate (respectively) an X-ray computed tomography (CT) image 10 of a cross-sectional view of an abdomen of an individual, a positron emission tomography (PET) image 12 of the abdomen of the same individual, and a composite image 14 generated from the CT and PET images. The CT image 10 of FIG. 1A illustrates some typical anatomic features with no apparent medical conditions. The PET image 12 of FIG. 1B illustrates the location and concentration of a radiolabelled substance that may be indicative of specific metabolic activity, which may be of clinical value in certain scenarios, such as oncology. The PET image of FIG. 1B 12 may provide some general information as to anatomic features (e.g., the general position of a concentrated radiolabelled substance, such as in the upper-left quadrant of a cross-sectional slice around the fifth thoracic disc), but the coincidence of the data in the PET image 12 of FIG. 1B with the data in the CT image 10 of FIG. 1A may be difficult to evaluate. By contrast, the composite image 14 of FIG. 1C illustrates the coincident data (such as generated by the techniques discussed herein), which reveals a specific anatomic feature with a distinctive appearance. This anatomic feature, which may represent a tumor or other abnormality, may not have been apparent from the CT image 10 of FIG. 1A or the PET image 12 of FIG. 1B, or from a side-by-side comparison of the images. The distinctiveness of this feature may only become apparent from the coincident data presented in the CT image 10 of FIG. 1A and the PET image 12 of FIG. 1B, as illustrated in the composite image 14 of FIG. 1C. The composite image 14 may therefore be useful to identify the proximity and spatial relationship of various anatomic structures. For example, the tumor may be visible in a first modality, but not in a second modality, whereas surrounding tissue may be visible in the second modality but not the first modality; and the composite image may better illustrate the positioning of the tumor with respect to the surrounding tissue than may be discerned from a side-by-side comparison of the images.

Thus, composite images generated from two or more images may present information of significant clinical value. Composite images of this type may be generated from different modalities, such as the CT image 10 of FIG. 1A and the PET image 12 of FIG. 1B. The composite images may also be generated to illustrate changes over time, and may be generated from images utilizing the same or different imaging modalities. For example, a composite image may show changes in an anatomic feature over a period of time, or a pre-operative vs. a post-operative view of the anatomic feature. Many such scenarios for generating and using composite images may be devised by those of ordinary skill in the art of medical imaging.

Figure 2A:
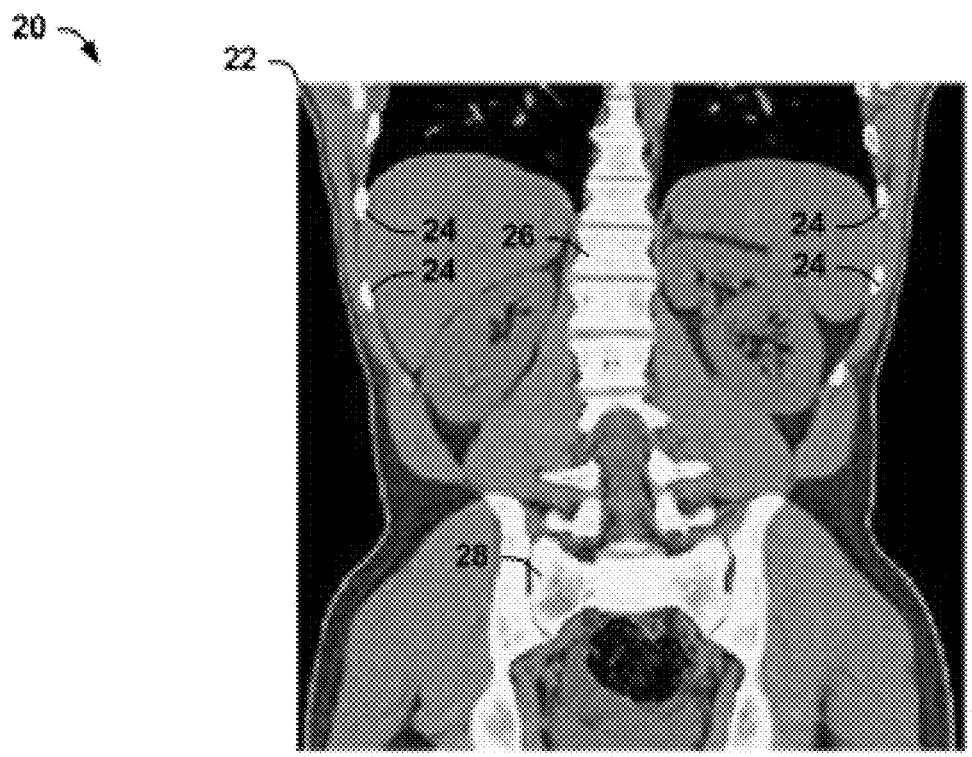
FIG. 2A is an X-ray computed tomography (CT) coronal plane cross-section image of an abdomen of an individual.
Figure 2B:
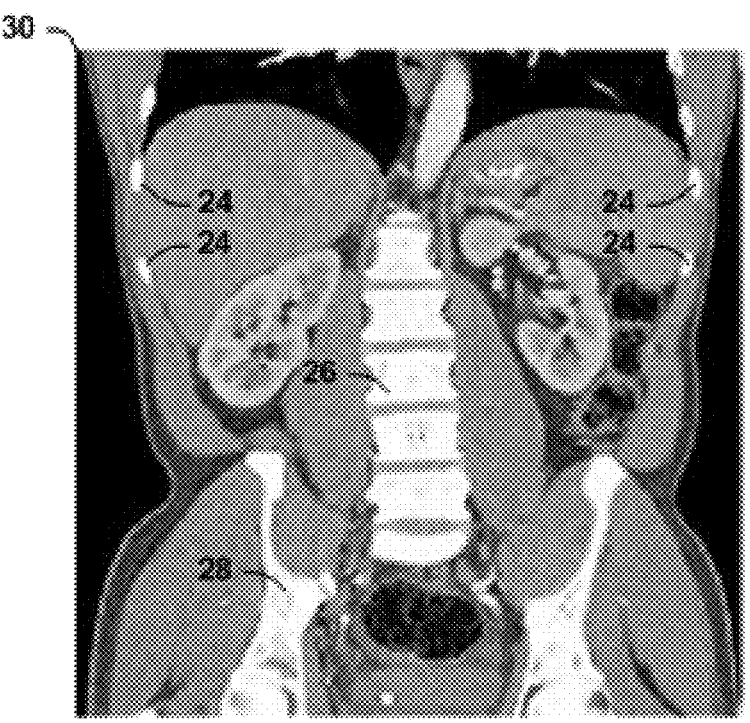
FIG. 2B is another X-ray computed tomography (CT) coronal plane cross-section image of the abdomen of the individual presented in FIG. 2A.
Figure 3:
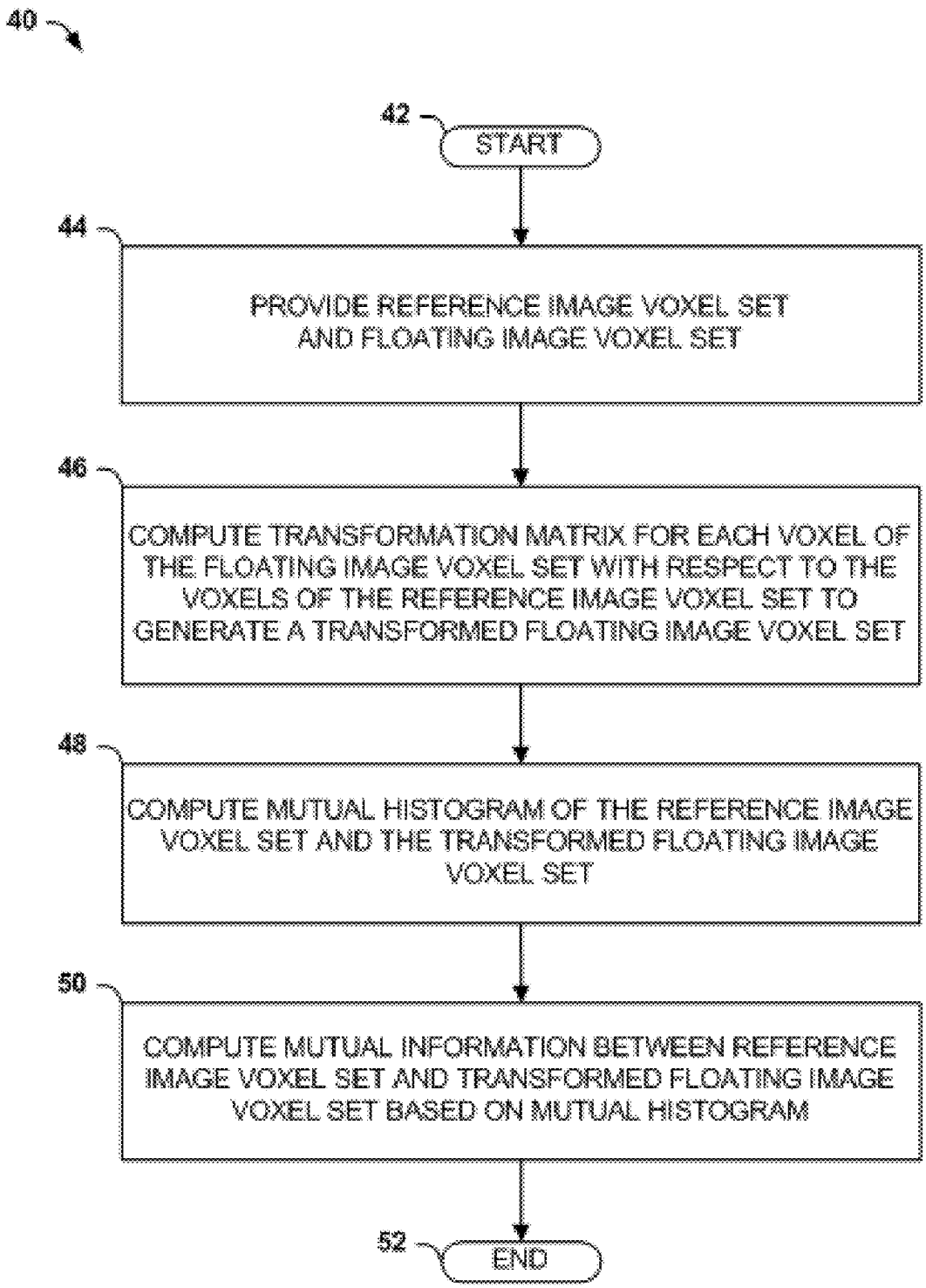
FIG. 3 is a flowchart illustrating a mathematical technique for performing nonrigid image registration.

However, the registration of medical images may be computationally difficult due to the soft tissue deformation between the images, such as when soft tissue is differently positioned, stretched, compressed, twisted, etc. in one image as compared with the other. As one example, FIGS. 2A and 2B illustrate two X-ray computed tomography (CT) scans 20 of the abdomen of an individual taken at two different times. It will be appreciated by comparison of the first image 22 of FIG. 2A and the second image 30 of FIG. 2B that the individual is differently positioned at the time of these images 20, such that the ribs 24, spine 26, and pelvis 28 of the individual are differently oriented due to soft tissue deformation (e.g., different muscle and tendon orientations in which the individual is positioned in each image.) Therefore, it may be difficult to combine the information from these images 20 to produce a composite image or a joint analysis of the different images. Even if registration is performed based on rigid points in each image 22, 30, such as the ribs 24, spine 26, and pelvis 28, the registration may inaccurately correlate different tissue points due to the soft tissue deformation, resulting in an inaccurate composite image or analysis. Thus, the accurate coincidence of information presented in the composite image 14 of FIG. 1C may be badly compromised unless the composite image generation process can adapt the information to account for differences in anatomic shapes and positioning. Mathematical models have been devised for registering images of rigid and soft tissue structures that account for soft tissue deformation. One such mathematical model is illustrated in the flowchart of FIG. 3, which illustrates an exemplary method 40 of performing a single-pass image registration of a floating image to a reference image. The exemplary method 40 begins at 42 and involves providing a reference image voxel set representing the reference image, and a floating image voxel set representing the floating image 44. The voxel sets may be of any dimensions, but are advantageously selected of the same dimensions for the floating image voxel set as for the reference image voxel set. The exemplary method 40 also involves calculating a coordinate transformation for the floating image voxels with reference to the voxels of the reference image voxel in the neighborhood of the transformed floating image voxel 46. The transformation may be calculated as a matrix multiplication of the reference image voxel coordinate with the transformed floating image voxels. The exemplary method 40 also involves computing the partial mutual histogram between the reference image voxel set and the transformed floating image voxel set 48. Because the transformed voxels of the floating image voxel set may correlate with only a portion of a reference image voxel, the floating image voxels may be interpolated by various techniques, and the mutual histogram contribution of each transformed floating image voxel may be distributed over several voxels in the reference image voxel set (e.g., based on a partial volumetric interpolation that weights each contribution by the volumetric percentage of the transformed floating image voxel that overlaps the reference image voxel.) (It may be appreciated that this interpolation may vary among implementations; e.g., in some implementations, each reference voxel may be transformed and distributed over a neighborhood of voxels in the floating image voxel set. Such embodiments might be more efficient, e.g., by maintaining the accessing of the reference image voxel set in a sequential order and on a regular coordinate system, instead of dealing with interpolations to a neighborhood of voxels in the reference image voxel set according to the differently oriented transformed floating image voxel set. Regardless of the selected implementation, the interpolation of the reference image voxel set and the transformed floating image voxel set may be equivalently performed.) The partial mutual histogram for each reference image voxel may be computed and aggregated to produce the mutual histogram for the reference image and the transformed floating image. Upon completing the computation of the mutual histogram 48, the exemplary method 40 involves computing the mutual information between the reference image and the transformed floating image, based on the mutual histogram 50. The mutual information calculation may be used as an indicator of the accuracy of the single-pass image registration. Having achieved a single pass of an image registration of the floating image with the reference image, the exemplary method 40 ends at 52.

The exemplary method 40 illustrated in FIG. 3 may provide a more accurate image registration model than rigid-body image registration techniques. The accuracy may be improved by performing two or more iterations of the image registration, where the transformed floating image voxel set produced by one iteration is used as the floating image voxel set provided to the next iteration. Successive iterations may be performed until a goal state is reached. In one embodiment, a specific number of iterations may be performed, or until a certain amount of processing time has been consumed. In a second embodiment, the iterative processing may continue until the accuracy of the registration exceeds a predefined threshold (e.g., a predefined mutual information score.) In a third embodiment, the iterative processing may continue until the detected improvement in accuracy (e.g., the amount of mutual information between the reference image and the transformed floating image) does not significantly improve with respect to prior iterations. In a fourth embodiment, the system may display the output of the iterative processing for a user, and may terminate upon receiving user input requesting termination of the iterative processing (e.g., when the user is satisfied with the image.) Other techniques for monitoring and controlling the progress of the iterative processing system may be devised by those of ordinary skill in the art while implementing the concepts described herein.

While iterative processing may improve the output of the technique, even greater improvements may be realized by performing successive passes of the image registration technique, wherein the image registration control unit modifies the reference image voxel set and the floating image voxel set between passes to produce different image registrations in different passes. One or more registration iterations may be performed during one pass, and the voxel sets may be modified again before commencing the registration iterations comprising the next pass. As one example, the floating image voxel set may be analyzed according to various subdivisions of voxels, where the voxels comprising a subdivision are analyzed together, such that one transformation is applied to all voxels in the subdivision. It may be advantageous to begin the multi-pass image registration with a coarse granularity of the voxel subdivision, e.g., by first processing all of the voxels together as one subdivision and evaluating one transformation for all voxels. This first evaluation may provide a gross adjustment, and may resemble a rigid body image registration technique. The multi-pass image registration may then be performed on successively finer-granularity voxel subdivisions, such that ever-smaller voxel subdivisions may be more precisely aligned with local features through smaller coordinate transformations.

Figure 4A:
FIGS. 4A-4D are illustrations of voxel sets manipulated in accordance with the techniques discussed herein.
Figure 4A:
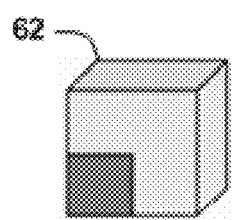
Figure 4B:
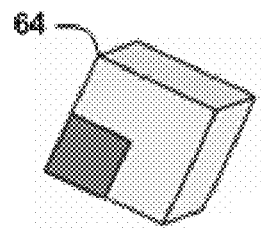
Figure 4C:
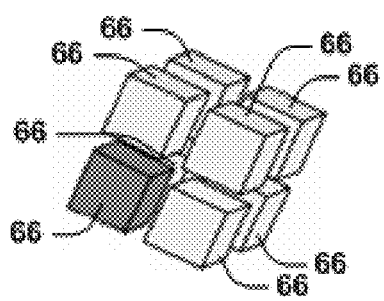
Figure 4D:
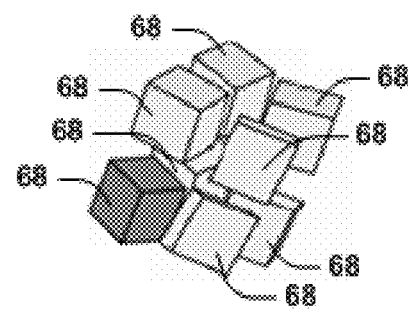

FIGS. 4A-4D together illustrate an example 60 of a multi-pass image registration with varying floating image voxel set subdivision granularity. In FIG. 4A, the image registration begins with a 1×1×1 voxel subdivision 62 of the floating image voxel set, which is initially represented with a non-transformed orientation. The image registration aligns the single voxel subdivision 62 (representing the entire floating image) with the reference image and applies a single transformation to all of the voxels in the floating image set to produce the transformed floating image voxel set 64 illustrated in FIG. 4B. (However, as discussed herein, some implementations of these techniques may align a single voxel subdivision of the reference image voxel set with a neighborhood of voxels in the transformed floating image voxel set; although the performance and implementation details may vary, these techniques achieve equivalent alignment results.) This alignment may be performed one or more times before moving on to the second pass, which begins by subdividing the voxels of the floating image voxel set into 2×2×2 subdivisions, i.e. eight subdivisions 66, such as illustrated in FIG. 4C. In this second pass, the voxels of the eight floating image voxel subdivisions 66 are analyzed with respect to the reference image voxel set, and a transformation is generated for each subdivision of the floating image voxel set and applied to all voxels represented thereby. In this manner, the architecture applies smaller coordinate transformations to the smaller granularity voxel subdivisions of the floating image voxel set, thereby producing eight transformed floating image voxel sets 68 that have been aligned with a smaller granularity and greater precision with the information of the reference image in the locale of the floating image subdivisions 68, as illustrated in FIG. 4D. The second pass may again comprise one or more iterations, and may in turn be followed by a third pass, which begins by further subdividing the floating image into 4×4×4 voxel subdivisions (i.e., 64 subdivisions), and so on. The precision of the image registration per voxel may be appreciably increased with each such pass. However, the cubic exponential growth of the voxel sets causes subsequent passes to become much more computationally complex; e.g., the eighth pass might involve 256×256×256 voxel subdivisions, thereby performing a computationally intensive image registration of 1.6 million floating image voxel set subdivisions. Thus, a tradeoff may be considered between the improved accuracy of a pass of the image registration and the computational requirements of the pass.

Figure 5:
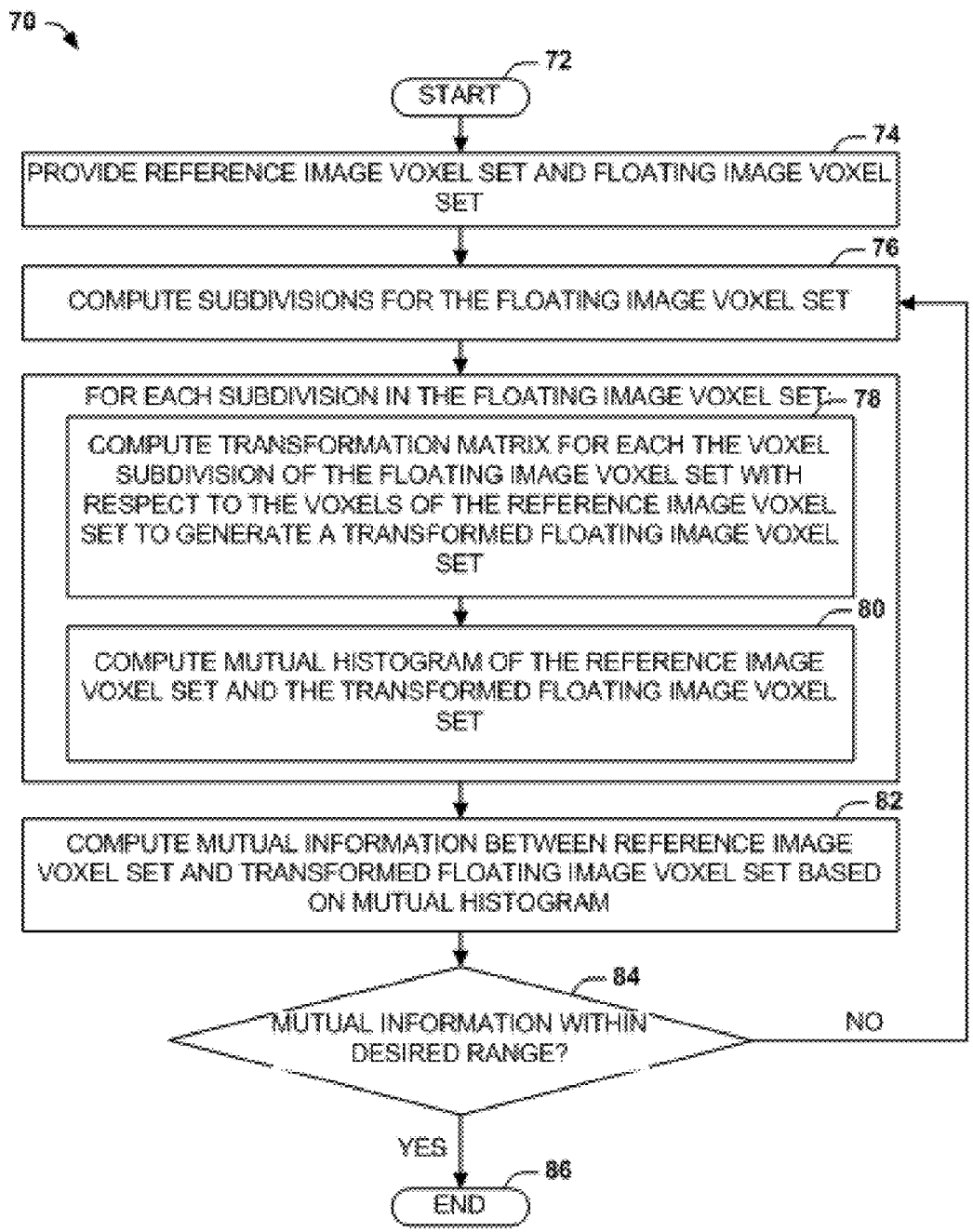
FIG. 5 is a flowchart illustrating another mathematical technique for performing nonrigid image registration.

FIG. 5 illustrates an exemplary multi-pass method 70 that implements this voxel subdivision technique for nonrigid image registration. The method of FIG. 5 again begins at 72 and involves providing a reference image voxel set and a floating image voxel set 74. The exemplary method 70 also involves subdividing the floating image voxel set into voxel subdivisions that are processed together 76. In the example noted above, the subdivisions may be chosen in the first pass as a single subdivision (comprising all of the voxels of the reference image voxel set and the floating image voxel set, and thereby resembling a rigid body image registration), and for subsequent passes as 2×2×2 octets of the subdivisions of the preceding pass.

After the subdivisions are computed, the exemplary method 70 involves processing of each subdivision of the floating image voxel set in multi-pass fashion. First, for each subdivision of the floating image voxel set, a transformation is computed with respect to the reference image voxel set and applied to each voxel in the floating image voxel set subdivision 78, thereby generating a transformed floating image voxel set. The exemplary method 70 also involves computing the mutual histogram for the reference image voxel set and the floating image voxel set 80. As before, where the transformed coordinates of the floating image voxel does not correspond precisely to a reference image voxel, the contribution of the transformed floating image voxel to the mutual histogram may be distributed over several reference image voxels based on interpolation (e.g., a partial volume interpolation.)

Once the multi-pass processing of each voxel subdivision of the floating image voxel set is complete, the exemplary method 70 involves calculating mutual information between the reference image voxel set and the floating image voxel set, based on the mutual histogram 82. The exemplary method 70 then involves assessing whether the mutual information is within a desired range. If so, then the image registration may be considered acceptably accurate, and the exemplary method 70 may therefore end at 86. However, if the mutual information is not yet within a desired range, the image registration may be performed again by returning to the subdivision computation 76, using the transformed floating image voxel set as input and generating a second transformed floating image voxel set. In accordance with the voxel subdivision technique noted above, the subdivisions in the subsequent passes may be formulated as octets of the previous pass (e.g., the second pass may operate on 2×2×2 or eight voxel subdivisions of the floating image voxel set; the third pass may operate on 4×4×4 or 64 voxel subdivisions; etc.) However, alternative formulations are possible; e.g., the voxel sets may utilize the same subdivisions, but comprising different voxels based on the transformed coordinates of the floating image voxels from the previous pass.

These mathematical models may be capable of registering medical images while accounting for the elastic deformation of soft tissue structures in one image with respect to the other. However, these mathematical models may be computationally complex, and may exceed the time available to the medical practitioners, thereby diminishing the utility of the mathematical models. For example, a software implementation of one such model may require 3.6 hours to register two images; but where one of the images may be generated intraoperatively, the medical practitioner may be unable to wait more than a few minutes for image registration.

However, some implementations of these mathematical models may be devised that accelerate the computational process, and therefore reduce the computational time to a more acceptable period, such as a six-minute image registration process. These implementations may include, e.g., specialized hardware that is configured to perform certain portions of the techniques in an improved manner, such as by parallel access to relevant information. Accordingly, some architectures are presented that may be capable of performing nonrigid image registration in at least a near-realtime manner, which may improve the utility of the mathematical techniques for medical use.

Figure 6:
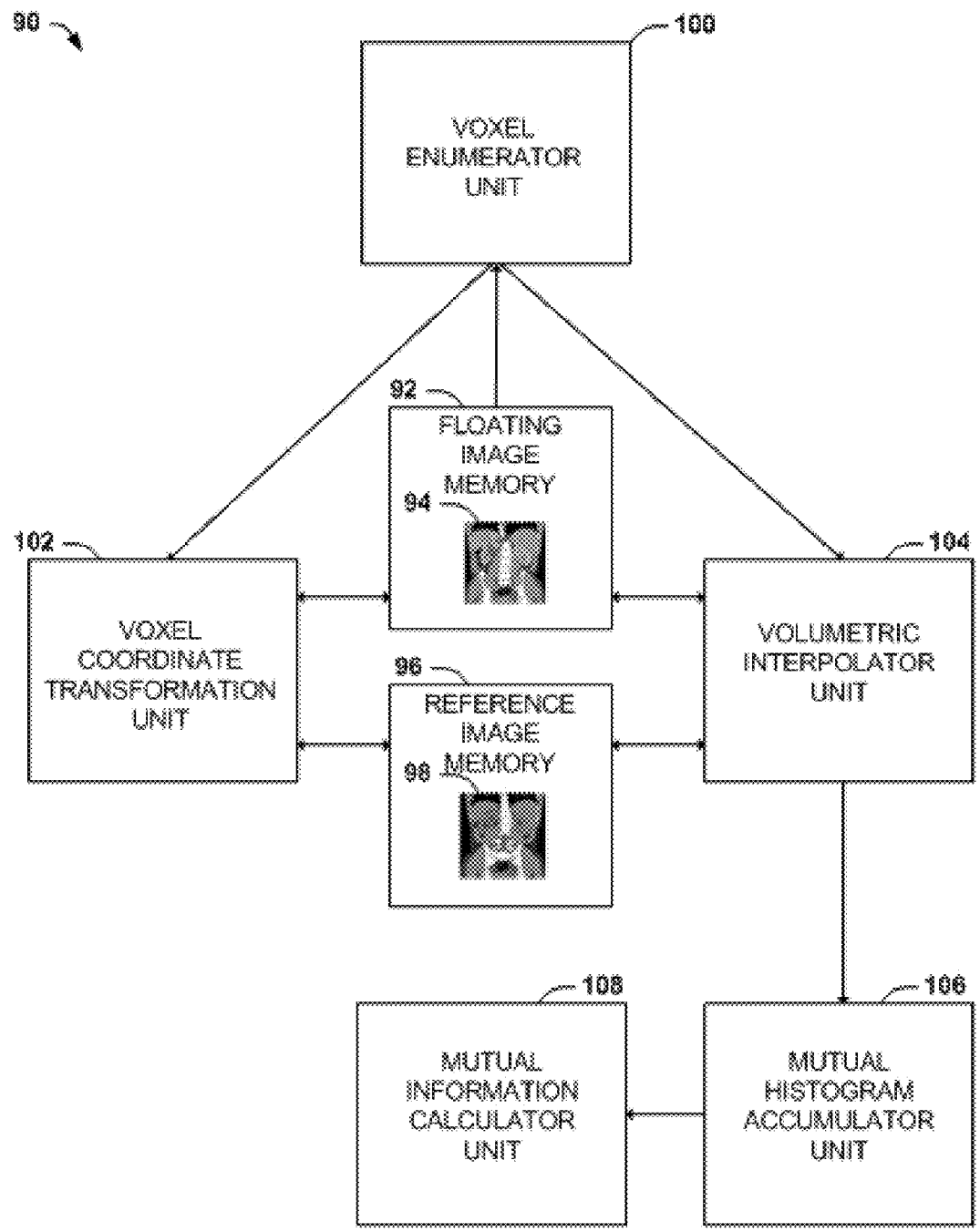
FIG. 6 is a component block diagram illustrating an exemplary system for performing near-realtime image registration.

An exemplary architecture 90 of this nature is displayed in FIG. 6, which presents a component block diagram of a system for registering a floating image with a reference image. Here and elsewhere herein, the usage of the terms "floating image" and "reference image" indicates that the registration is being performed by transforming the floating image to match the reference image, e.g., for the purpose of maximizing mutual information.

The exemplary system of FIG. 6 comprises a floating image memory 92, which is configured to store a floating image voxel set 94 representing the floating image, and a reference image memory 96, which is configured to store a reference image voxel set 98 representing the reference image. The floating image voxel set 94 and the reference image voxel set 98 may comprise any number of voxels, e.g., a 16×16×16 voxel set or a 64×128×256 voxel set. It may be advantageous to the techniques discussed herein to store the reference image voxel set 98 with the same dimensions as the floating image voxel set 94.

The exemplary system 90 also comprises a voxel enumerator unit 100, which is configured to enumerate the voxels in sequential order along an axis of the floating image voxel set 92. For example, if the floating image voxel set 98 comprises 16×16×16 voxels, the voxel enumerator unit 100 may be configured to enumerate each Z-axis voxel in the floating image voxel set 94 for each Y-axis voxel, and to enumerate each Y-axis voxel in the floating image voxel set 94 for each X-axis voxel. This nested enumeration may be better understood with reference to the following pseudocode:

```
for (x = 0; x < floating_image_voxels.x_size; x++) {
    for (y = 0; y < floating_image_voxels.y_size; y++) {
        for (z = 0; z < floating_image_voxels.z_size; z++) {
            process_voxel(floating_image_voxels[x, y, z]);
        }
    }
}
```

However, it will be appreciated that the order of the axes over which the voxel enumerator unit 100 operates may vary; e.g., the voxel enumerator unit 100 may instead enumerate over the X-axis voxels for each Y-axis voxel, and each Y-axis voxel for each Z-axis voxel. Again, it may be appreciated that some embodiments may iterate over the voxels of the reference image voxel set and align each voxel with a neighborhood of voxels in the transformed floating image voxel set; although the implementation and performance details may vary, these variant techniques produce equivalent registration results.

The exemplary system of FIG. 6 also comprises a voxel coordinate transformation unit 102, which is configured to transform the voxels of the floating image voxel set 92 indicated by the voxel enumerator unit 100 with respect to the voxel in the reference image voxel set 98 and to produce a transformed floating image voxel set. In accordance with the mathematical techniques described above, the voxel coordinate transformation unit 102 selects the voxel neighborhood of the reference image voxel set 98 that corresponds to the voxel of the floating image voxel set 94 that is indicated by the voxel enumerator unit. 100 While any size neighborhood may be selected with respect to a voxel in the floating image voxel set 94, it may be computationally efficient to select a small neighborhood, e.g., the 2×2×2 voxel neighborhood in the reference image voxel set 98 with respect to the voxel in the floating image voxel set 94. For the voxels in the selected voxel neighborhood, the voxel coordinate transformation unit 102 produces a transformed coordinate based on the mathematical techniques described above. The transformed coordinate for the voxels in the floating image voxel set 94 is stored in the floating image memory 92, thereby comprising a transformed floating image voxel set.

The exemplary system 90 of FIG. 6 also comprises a mutual histogram accumulator unit 106, which is configured to accumulate a mutual histogram 106 representing the transformed floating image voxel set interpolated with the reference image voxel set 98. In accordance with the mathematical techniques described hereinabove, the mutual histogram represents the histogram of the floating image voxel set 94 transformed and registered with the reference image voxel set 98, which serves as a metric for the accuracy of the registration based on the mutual information of the composite image. The mutual histogram is generated by comparing the voxels of the reference image voxel set 98 with the voxels of the transformed floating image voxel set 94. In the exemplary system 90 of FIG. 6, the mutual histogram accumulator unit 104 stores the mutual histogram data for each voxel in the reference image voxel set 98 by accumulating the histogram values of each interpolated voxel in the transformed floating image voxel set 94 corresponding to the reference image voxel set 98.

This computation includes the transformation of the coordinates of the voxels of the transformed floating image voxel set 94 to correspond to the coordinates of the voxels of the reference image voxel set 98. Therefore, the exemplary system of FIG. 6 comprises a volumetric interpolator unit 104, which is configured to store in the mutual histogram accumulator unit 106 the contribution to the mutual histogram of respective voxels of the transformed floating image voxel set 94 interpolated with respective voxels of the reference image voxel set 98. Whereas the mutual histogram accumulator unit 106 stores the mutual histogram data for each voxel in the reference image voxel set 98, the volumetric interpolator unit 104 calculates this histogram data based on the interpolated values of the voxels in the transformed floating image voxel set 94 corresponding to the reference image voxel set 98. Stated another way, for each voxel in the transformed floating image voxel set 94, the volumetric interpolator unit 104 determines the voxels in the registered image voxel set 98 having coordinates that partially or wholly match the coordinate of the transformed floating image voxel, compares the value of each matching transformed floating image voxel to the value of the reference image voxel, and weights the comparison based on the magnitude of the correspondence between the transformed coordinate of the floating image voxel with the reference image voxel. This computation forms the basis of the interpolated contribution of this transformed floating image voxel to the mutual histogram, and the volumetric interpolator unit 104 stores this computed data in the mutual histogram accumulator unit 106 for the reference image voxel. Accordingly, once the voxel enumerator unit has enumerated all of the voxels in the reference image voxel set, the mutual histogram accumulator unit 106 contains the accumulated mutual histogram values of the interpolated voxels of each voxel of the floating image voxel set 94 and the neighboring voxels in the reference image voxel set 98; i.e., the mutual histogram accumulator unit 106 contains a full mutual histogram for the transformed floating image registered with the reference image.

The exemplary system 90 of FIG. 6 also comprises a mutual information calculator unit 108, which comprises a configuration to calculate the mutual information between the reference image voxel set 98 and the transformed floating image voxel set 94 based on the mutual histogram. The mutual information calculator unit 108 performs a statistical calculation of the mutual histogram in order to determine the mutual information shared by the reference image and the transformed floating image, which represents an indicator of the accuracy of the image registration. If the mutual information reported by the mutual information calculator unit 108 is within a desired range of accuracy, then the exemplary system 90 may conclude the image registration process. On the other hand, if the mutual information reported by the mutual information calculator unit 108 is not yet within a desired range, then the exemplary system 90 may be configured to perform additional passes of the image registration in order to achieve improved accuracy.

Architectures configured to perform near-realtime non-rigid image registration, such as the exemplary system 90 of FIG. 6, may be useful for image registration between two images. As one example, a preoperative image may be registered with an intraoperative image. Preoperative PET imaging may be particularly suitable for this image registration. PET imaging data can provide sensitive and accurate detection of abnormal tissues, such as tumors; however, the PET imaging process is time-consuming and involves radioactive compounds to which individual exposure should be limited. Accordingly, PET images are rarely generated intraoperatively, and it may be helpful to provide a composite image of preoperative PET data and an intraoperative image, such as a CT or MRI image. Moreover, the production of such a composite image with near-realtime performance may be advantageous for the time-sensitive scenario of intraoperative imaging, where the imaging data will be immediately utilized by the healthcare providers. More generally, these architectures may be useful for providing near-realtime image registration for any types of images, such as an intraoperative image (e.g., intraoperative X-ray, CT, ultrasound, or MRI) with a pre-operative image (e.g., preoperative PET); an intraoperative image (e.g., before tissue resection) with another intraoperative image (e.g., after tissue resection); or a preoperative image (e.g., a contrast-enhanced image) with another preoperative image (e.g., a non-contrast-enhanced image.) Moreover, multiple images may be registered with each other in serial and/or parallel. For example, registering an MRI image with a CT image, and also (before, after, or simultaneously) registering the same CT image with a PET image, may indirectly register the MRI image with the PET image.

Architectures devised to apply these image registration techniques, such as the exemplary system 90 of FIG. 6, may be advantageously configured to accelerate the computational processing in order to provide near-realtime image registration. For example, whereas a conventional software implementation on ordinary computing hardware may require several hours to perform a nonrigid image registration of two 256×256×256-voxel images, another system may be devised to perform the same registration in only a few minutes, which may provide near-realtime image registration that is advantageous in time-critical scenarios (e.g., for generating a composite image using one or more intraoperative images.)

One architectural feature that may facilitate such accelerated computational processing relates to the configuration of the reference image memory and the floating image memory. One relevant aspect of this computational process is the manner in which the voxel data of the reference image voxel set and the floating image voxel set are accessed. During the image registration process, the voxels of the reference image voxel set are enumerated in a predictably sequential order (e.g., in sequence along each axis of the voxel data set, as indicated by the voxel enumerator unit.) Accordingly, these voxels may be fetched in a pipelined manner, such as by a read-ahead memory cache that can predict and prefetch the next voxels to be read from the reference image voxel set. However, the respective voxels of the floating image voxel set that comprise the voxel neighborhood of each reference image voxel are fetched in a random-access manner, which imposes a considerable memory constraint on the floating image memory. It may be more difficult to predict the floating image voxels that will next be needed by the computational process, and the amount of data representing the floating image voxel set may mitigate the benefits of memory caching. It has been determined in that in ordinary software implementations of these techniques, the memory accesses to the reference image voxel set and the floating image voxel set may be the primary processing bottleneck, and may therefore limit the speed of the image registration despite the computational power provided in the system architecture.

Accordingly, the performance of the image registration process may be improved by reducing this memory bottleneck based on the manner in which the voxel data is stored and accessed. One such technique relates to the memory storage of the voxels in a cubic addressing scheme, where the memory address of a voxel can be computed based on the coordinate of the voxel in the voxel space. Another technique relates to the configuration of the architecture to provide rapid access to the voxel data according to the usage of the voxel data sets. As one example, the exemplary system 90 of FIG. 6 is configured to enumerate the voxels of the reference image voxel set in sequential order along each axis. This configuration enables sequential memory access in the reference image memory, which may take advantage of memory pipelining and read-ahead memory caching, thereby providing a steady flow of voxel data from the reference image voxel set and accelerating the rate-limiting memory access to the reference image voxel set.

Another technique for improved memory access in these techniques relates to the burst mode architecture of many memory devices, wherein multiple data addresses may be read and produced in parallel in one read operation. For example, some memories, such as burst EDO RAM, are capable of providing burst-mode access to four addresses in parallel. Accordingly, while reading a voxel octet comprising the voxel neighborhood in the floating image voxel set with respect to a voxel in the reference image voxel set, the floating image memory may be accessed in burst mode to provide the first four voxels in the first burst operation, and the second four voxels in the second burst operation. Accordingly, it may be advantageous to configure the floating image memory to store at least four copies of the floating image voxel set, where each burst-mode access reads one voxel from each of the four floating image voxel sets. A floating image memory configured in this manner may therefore be able to read a voxel octet from the floating image voxel set corresponding to a voxel in the reference image voxel set.

Another aspect of the image registration techniques that may be varyingly embodied in different architectures relates to the interpolation technique applied by the volumetric interpolator unit. It may be appreciated that many such interpolation techniques may be suitable for interpolating the transformed voxels of the transformed floating image voxel set onto the voxels of the reference image voxel set. As one example, nearest neighbor interpolation may be used, wherein a small number (e.g., two) of transformed voxels of the floating image voxel set that are nearest a voxel in the reference image voxel set are selected for the mutual histogram. As another example, a trilinear interpolation technique may be used, wherein the precise coordinates of each vertex of the transformed floating image voxel are computed and compared with the coordinates of each voxel in the reference image voxel set. As still another example, a partial volumetric interpolation technique may be used, wherein a portion of each transformed floating image voxel corresponds to each voxel of the reference image voxel set, where the portion is based on the volumetric overlap of the transformed floating image voxel with the coordinate space of the reference image voxel. These and other interpolation techniques may be used, and various interpolation techniques may present different advantages. For example, some techniques may render more accurate interpolation but may be more computationally difficult, whereas other techniques may require less computation but may yield less accurate interpolation.

Still another aspect of the image registration techniques that may be varyingly embodied in different architectures relates to the mutual information calculation, such as embodied in the mutual information calculator unit in the exemplary system 90 of FIG. 6. The mutual image calculation may be performed based on the mutual histogram according to many statistical methods. One such method is an entropy probability distribution, which calculates the mutual information of the images based on the joint probabilities between the reference image voxel set and the transformed floating image voxel set as an aggregate of the individual probabilities of the reference image voxels with respective transformed floating image voxels. The individual probabilities may be calculated based on the formula:

$$f(p) = p \cdot \ln(p)$$

where p comprises the difference between the value of each reference image voxel and corresponding transformed floating image voxels weighted by degree of interpolation (e.g., by partial volumetric interpolation.) The sum of the individual probabilities between each reference image voxel and the corresponding transformed floating image voxels comprises the joint probability, which may be utilized as an entropy assessment representing the amount of mutual information shared by the reference image and the transformed floating image. This entropy assessment may be used to assess the accuracy of the image registration process, and may be compared with other image registrations (e.g., prior or subsequent image registrations based on these techniques.) For example, and similarly with the iterative processing techniques, the image registration process may be performed in a multi-pass manner, and may continue as long as subsequent passes provide improved entropy assessments with respect to prior passes, or until the entropy assessment falls within a desired range of accuracy.

The use of the entropy assessment provided above may be computationally difficult due to the logarithmic assessment of the probability value. The entropy assessment may therefore require the calculation of many logarithmic values for an image registration, which may computationally inefficient. Instead of computing the logarithmic component of the individual probabilities, an architecture that relies on this entropy assessment may be further configured to include a logarithmic lookup table in the mutual information calculator unit, and the mutual information calculator unit configured to consult the logarithmic lookup table to compute logarithmic components of the individual probabilities. The logarithmic lookup table values might be less precise than a full logarithmic calculation, but the accuracy of the logarithmic values thereby produced may be adequate for the individual probability calculations comprising the entropy assessment, and may therefore produce a computational acceleration while yielding an acceptable loss of precision in the entropy assessment.

The architectures described herein, such as the exemplary system 90 of FIG. 6, may be configured to perform an image registration of a floating image with a reference image. However, a single pass of the image registration process may provide inadequate results, and a better result may be achieved by performing successive passes of the image registration (and, optionally, multiple iterations within each pass) until a desired accuracy (e.g., a desired correlation of mutual information, such as measured by an entropy assessment) between the reference image and the transformed floating image is achieved. Accordingly, an architecture may include an image registration control unit, which is configured to perform multi-pass registration of the floating image with the reference image until the mutual information between the reference image voxel set and the transformed floating image voxel set is within a desired mutual information range. The image registration control unit may be operatively coupled with the other elements of the architecture, such as the voxel enumerator unit, voxel coordinate transformation unit, the mutual histogram accumulator unit, the volumetric interpolator unit, and the mutual information calculator unit, and may coordinate the execution of the image registration. Upon the completion of a pass of the image registration process, the image registration control unit may also reference the mutual information calculation (e.g., the entropy assessment) produced by the mutual information calculator unit, and may compare the calculation with a desired mutual information range, as may be specified by a system user or encoded in the image registration control unit by the architecture designer. If the pass of the image registration produces an acceptable sharing of mutual information, the image registration control unit may conclude the image registration process, such as by outputting the coordinates of the voxels comprising the transformed floating image, or by outputting a composite image of the reference image and the transformed floating image. However, if the pass of the image registration does not produce an acceptable sharing of mutual information, the image registration control module may initiate a subsequent pass of the image registration process based on the reference image and the transformed floating image provided by the previous pass, e.g., by again subdividing the voxel sets provided as input to the next pass. The image registration control unit may continue to perform subdivisions and passes of the image registration process until an acceptable entropy assessment is achieved, until the entropy assessments of subsequent passes are not noticeably improved with respect to entropy assessments of prior passes, until a maximum number of passes are performed, until the image registration process is interrupted by the system user, etc.

Image registration architectures may be devised that implement the voxel set subdivision technique described hereinabove. As one example, the reference image memory and the floating image memory may be initially loaded with a reference image voxel set and a floating image voxel set, respectively, having a coarse granularity (e.g., as a 1×1×1 voxel subdivision, such as illustrated in FIG. 4A.) The registration control unit may be configured to initiate the first pass of the image registration with this coarse granularity. Upon completing the first pass, the registration control unit may be configured to subdivide the voxels of the transformed floating image voxel set before initiating a second or subsequent pass of the image registration. The resulting architecture may therefore provide a multi-pass image registration process (having one or more registration iterations per pass) on increasingly finer-granularity floating image voxel set subdivisions as described herein.

An architecture configured to perform the image registration in a multi-pass manner may be advantageously designed to reuse some information between passes. As one example, the calculation of the mutual histogram for a pass may utilize the mutual histogram information from a previous pass. An exemplary architecture is illustrated in FIGS. 7A-7B, which illustrate, respectively, a component block diagram of a mutual histogram accumulator unit 110 that may be included in an image registration system and a flowchart 120 illustrating the operation of such a mutual histogram accumulator unit in the image registration process.

Figure 7A:
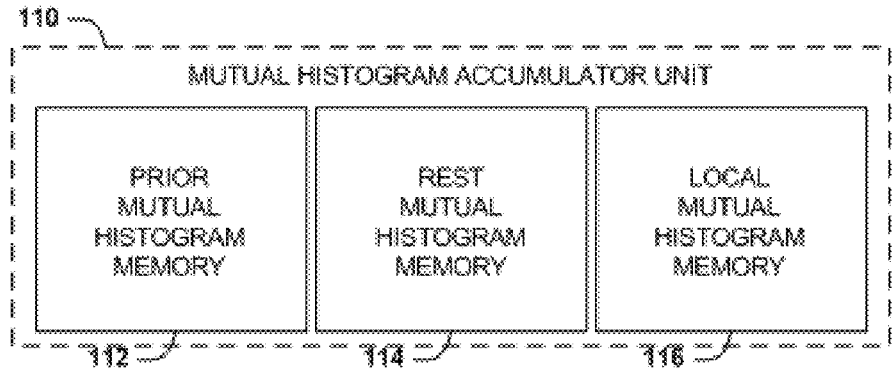
FIG. 7A is a component block diagram illustrating a mutual histogram accumulator unit for use in systems for performing near-realtime image registration.

The mutual histogram accumulator unit 110 illustrated in FIG. 7A comprises three memories. The prior mutual histogram memory 112 comprises an array representing the mutual histogram generated during a prior pass of the image registration, i.e., the mutual histogram of the combined reference image and transformed floating image from which the voxel sets used in the current pass derive. The rest mutual histogram memory 114 comprises an array representing the mutual histogram accumulated during the current pass of the image registration. The local mutual histogram memory 116 comprises the contribution of a voxel in the transformed floating image voxel set to the mutual histogram.

Figure 7B:
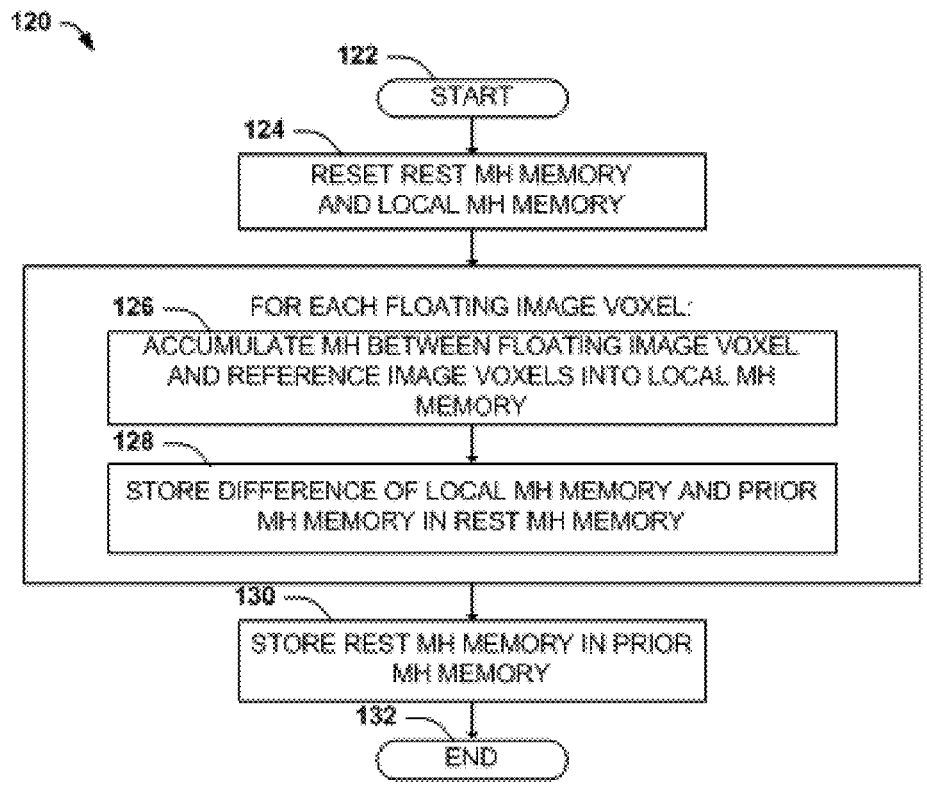
FIG. 7B is a flowchart illustrating a method of using the mutual histogram accumulator unit illustrated in FIG. 7A to compute a mutual histogram.

The mutual histogram accumulator unit 110 may compute the mutual histogram for a current pass by utilizing the prior mutual histogram memory 112, the rest mutual histogram memory 114, and the local mutual histogram memory 116 according to the method 120 illustrated in FIG. 7B. At the beginning of a pass (e.g., at the start 122 of the exemplary method 120 of FIG. 7B), the mutual histogram accumulator unit 110 resets 124 the local mutual histogram memory 116 and the array comprising the rest mutual histogram memory 114. In the first pass of the image registration, the prior mutual histogram memory 112 is initially empty, but in subsequent passes, the prior mutual histogram memory 112 stores the mutual histogram from the prior pass. Upon computing a coordinate transformation for the floating image voxel indicated by the voxel enumerator unit, the mutual histogram accumulator unit 110 computes the adjusted mutual histogram data in the following manner. First, the value differences between the floating image voxel and the reference image voxels (interpolated by the volumetric interpolation unit) are accumulated 126 in the local mutual histogram memory 112. Second, the mutual histogram value for the floating image voxel is computed 128 based on the difference between the accumulated local mutual histogram memory 116 and the value stored in the prior mutual histogram memory 112 for the floating image voxel, and this computed mutual histogram value is stored 130 in the rest mutual histogram memory 114 for the reference image voxel. When the voxel enumerator component has enumerated all of the voxels in the floating image voxel set, the rest mutual histogram memory 114 will represent the mutual histogram of the reference image voxel set and the transformed floating image voxel set. This mutual histogram may then be stored in the prior mutual histogram memory 112 for use in a subsequent pass. Having generated the mutual histogram for the current pass of the image registration and having stored the mutual histogram for use in the next pass, the exemplary method 120 employed by the mutual histogram accumulator unit ends at 132. By reusing the mutual histogram information from the previous pass, the mutual histogram accumulator unit 110 illustrated in FIG. 7A and operating according to the method illustrated in FIG. 7B achieves an improved computational performance as compared implementations that recompute the mutual histogram in each pass.

The techniques and components described hereinabove may be embodied in many implementations. However, it has been discovered that software implementations may be unable to perform as well as hardware implementations, such as hardware components configured to perform the various functions of these techniques, which may operate in parallel and with a configuration devised for the specifics of each function. For example, the mutual information calculator unit may be implemented as a software algorithm for computing entropy calculations using the general-purpose computation of the computing processor, including the logarithmic computation capabilities; but a hardware implementation specially configured to perform this calculation (e.g., by incorporating a logarithmic lookup table) may be capable of achieving better computational performance.

Figure 8:
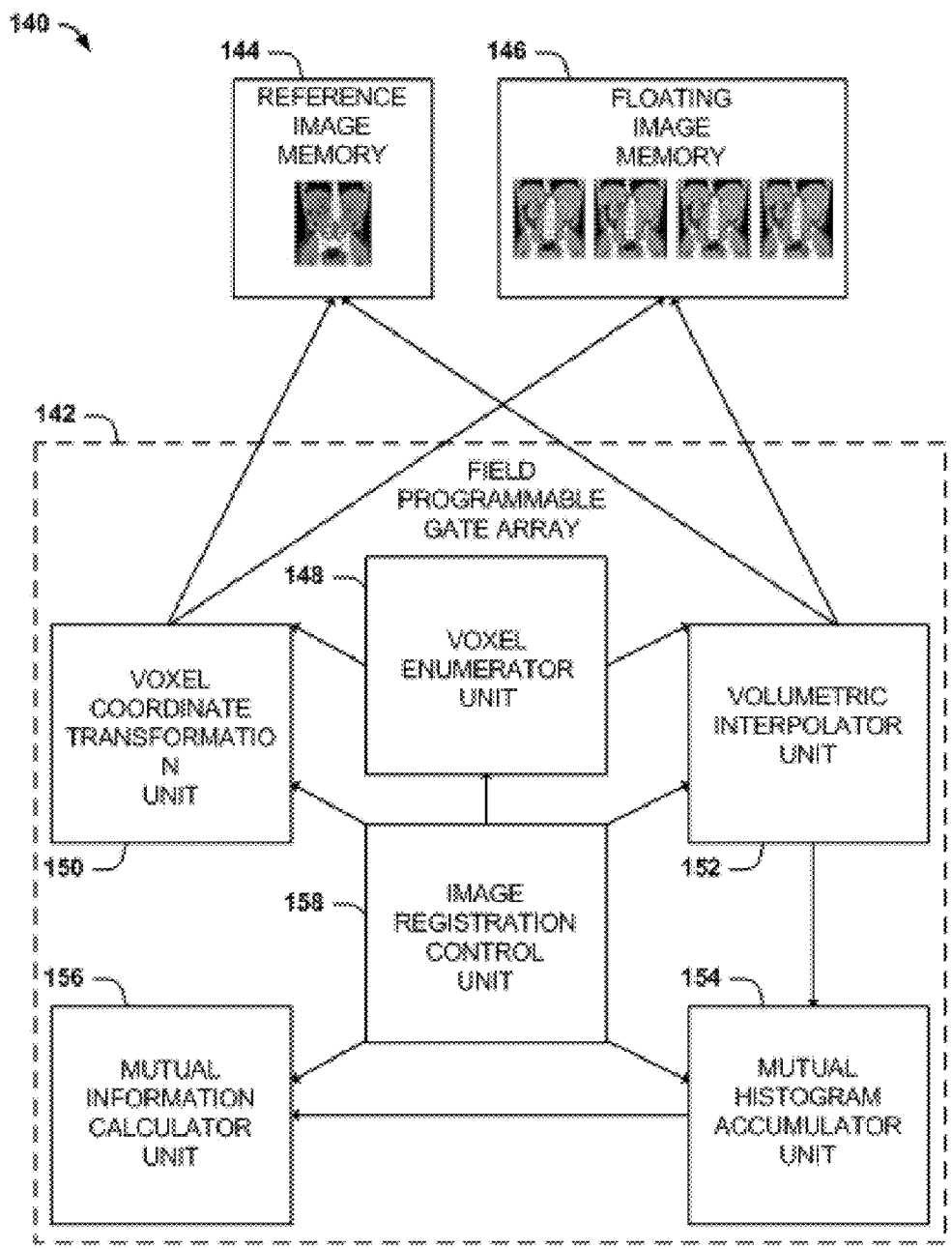
FIG. 8 is a component block diagram illustrating another exemplary system for performing near-realtime image registration.

An exemplary system 140 of this nature is illustrated in FIG. 8, wherein several of the components of such an architecture (such as the system of FIG. 6) are configured as a field-programmable gate array (FPGA) circuit 142, in which logical blocks of the circuit may be configured to perform the specialized computational processes required of each unit. In this embodiment, the reference image memory and the floating image memory comprise system memory, such as a SoDIMM memory array. As noted in the discussion of improved memory access techniques, the memories are configured to provide burst access to multiple memory addresses in parallel, and the floating image memory 146 is configured to store (at least) four copies of the floating image voxel set for parallel access to a voxel octet in a two-burst read. Also in this exemplary system 140, the volumetric enumerator 148, the volumetric coordinate transformation unit 150, the volumetric interpolation unit 152, the mutual histogram accumulator unit 154, and the mutual information calculator unit 156 are devised as components programmed on an FPGA circuit, where each task may be performed by a specialized hardware device instead of a general-purpose software algorithm. This exemplary system 140 also features an image registration control unit 158, which is operably coupled to the volumetric enumerator unit 148, the volumetric coordinate transformation unit 150, the volumetric interpolation unit 152, the mutual histogram accumulator unit 154, and the mutual information calculator unit 156 in order to coordinate the image registration and to provide a multi-pass image registration based on varying granularity of the voxel subdivisions. It may be appreciated that further improvements may be achieved through the use of higher-performance hardware and/or more heavily optimized software (e.g., a faster processor, additional processors and/or processors having multiple cores, memory with better throughout or lower latency, etc.)

The performance gains that may be achieved in hardware implementations (such as FPGA circuits) over software implementations are illustrated in FIGS. 9A-9B. The table 160 of FIG. 9A presents a comparison of the performance of the mutual information computation for successive passes of a test data set between a software implementation and an FPGA-based implementation. The implementations utilized the voxel subdivision technique discussed herein and illustrated in FIGS. 5A-5D, and each pass of the image registration dealt with variable size voxel subdivision representations of the reference image and the floating image, where each image comprises 256×256×256 voxels. For example, in the first pass, the entire image is evaluated as a single voxel subdivision (a 1×1×1 subdivision, comprising the 256×256×256 voxels) for both the reference image and the floating image (such as in FIGS. 7A-7B); hence, the mutual image calculation must be calculated across the entire image all of the voxels comprising the single subdivision. By contrast, in the fifth pass, the images are subdivided into 16×16×16 voxel subdivisions (each subdivision comprising 16×16×16 voxels), so each mutual image calculation pertains to only 0.2% of the image data. In this comparison, the FPGA-based implementation was able to accelerate the mutual image calculation between 20 and 41 times over the software implementation for various passes, illustrating a notable improvement in the performance of the image registration.

The table 170 of FIG. 9B represents a similar comparison of the overall performance of the image registration techniques between a software implementation and an FPGA-based hardware implementation. Two such evaluations were performed: registration of an intraoperative X-ray computed tomography (CT) image with a preoperative CT image, and registration of an intraoperative CT image with a preoperative positron computed tomography (PET) image. In both tests, the software implementation required over three hours to perform the image registration sequence, whereas the FPGA-based hardware implementation completed the same analysis in only six minutes. The latter implementation therefore provides a near-realtime image registration, which may be advantageous in time-critical scenarios, such as where one or both of the images are generated intraoperatively for immediate use in the medical or surgical procedure.

The techniques described herein are not limited to the embodiments illustrated of FIGS. 6 and 9; rather, these techniques may be embodied in a wide range of implementations having various aspects and advantages. One such alternative embodiment is the exemplary system 180 illustrated in FIG. 10. Similar to previously discussed implementations, this exemplary system 180 features a reference image memory 182 and a floating image memory 184, as well as a voxel enumerator unit 186, a voxel coordinate transformation unit 188, a volumetric interpolation unit 190, a mutual information calculator unit 192, and a mutual histogram accumulator unit 194. As will be appreciated based on the foregoing discussion, this exemplary system 180 also features an image control unit 196 that is operably coupled with the voxel enumerator unit 186, the voxel coordinate transformation unit 188, the volumetric interpolation unit 190, the mutual information calculator unit 192, and the mutual histogram accumulator unit 194, so as to coordinate the operation of the image registration in a multi-pass manner.

Figure 10:
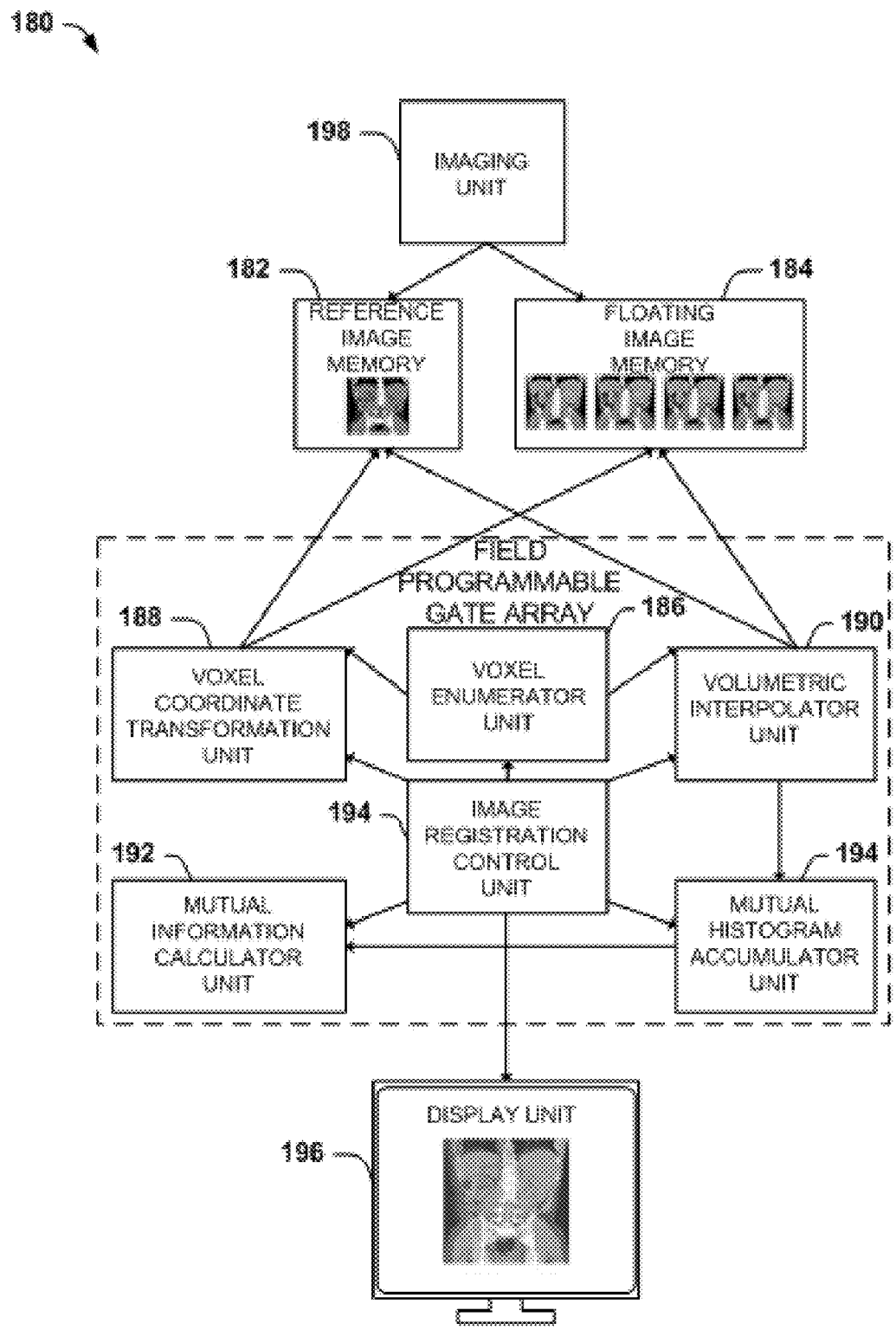
FIG. 10 is a component block diagram illustrating yet another exemplary system for performing near-realtime image registration.

In addition to these elements, the exemplary system 180 of FIG. 10 is also configured with a display unit 196, which is configured to display the reference image voxel set combined with the transformed floating image voxel set, i.e., a composite of the reference image and the registered floating image. The composite image may be generated in many ways, such as by combining the image data for each voxel in the reference image voxel set with the corresponding voxels of the transformed floating image voxel set (and where such corresponding voxels are weighted based on a desired interpolation, e.g., by partial volume interpolation), or by displaying a semi-transparent transformed floating image over a semi-transparent reference image. Such composite images may be used to illustrate aspects of the individual's anatomy that present a distinctive appearance in multimodal imaging, which may be more distinctive and more helpful for diagnosis and/or therapy than single-modality imaging. The exemplary system 180 of FIG. 10 also comprises an imaging unit 198, which is configured to generate at least one of the reference image and the floating image. As one example, the imaging unit 198 may be a PET imaging apparatus configured to generate preoperative PET images and to store the PET images in the floating image memory 184 for image registration with intraoperatively captured images. As another example, the imaging unit 198 may be an intraoperative CT apparatus configured to generate intraoperative CT images and to store the CT images in the reference image memory 182 for image registration with preoperatively captured images.

These techniques of performing the deformable tissue image registration perform the computationally difficult process of aligning the voxels of the floating image with the voxels of the reference image in order to enable an anatomically coincident illustration of the imaged portion of the individual. Once the registration is complete, a composite image may be generated by combining the voxels of the reference image voxel set with the voxels of the transformed floating image voxel set. For example, the composite image may comprise the average of each voxel of the reference image voxel set and the corresponding voxels of the transformed floating image voxel set. Multiple such voxels of the transformed floating image voxel set may coincide with a voxel in the reference image voxel set, and may overlap only a portion of the reference image voxel; therefore, the average may be weighted by the degree of overlap of each transformed floating image voxel with the reference image voxel. Other techniques for combining the image data may be devised by those of ordinary skill in the art while generating the composite image in accordance with the techniques disclosed herein.

An understanding of the foregoing techniques (including the computer-implemented methods and the systems related thereto) may yield an appreciation for a technique of generating a composite image from a reference image voxel set and a floating image voxel set. Furthermore, a review of FIGS. 1A-1C may yield an appreciation for the information that may be revealed by a composite image that may be less apparent from the reference image and the floating image that comprise the composite image. It may therefore be appreciated that the use of the techniques provided herein may be advantageously applied in the practice of medicine, such as in the performance of a medical procedure on the individual having the anatomy shown in the composite image.

Figure 11:
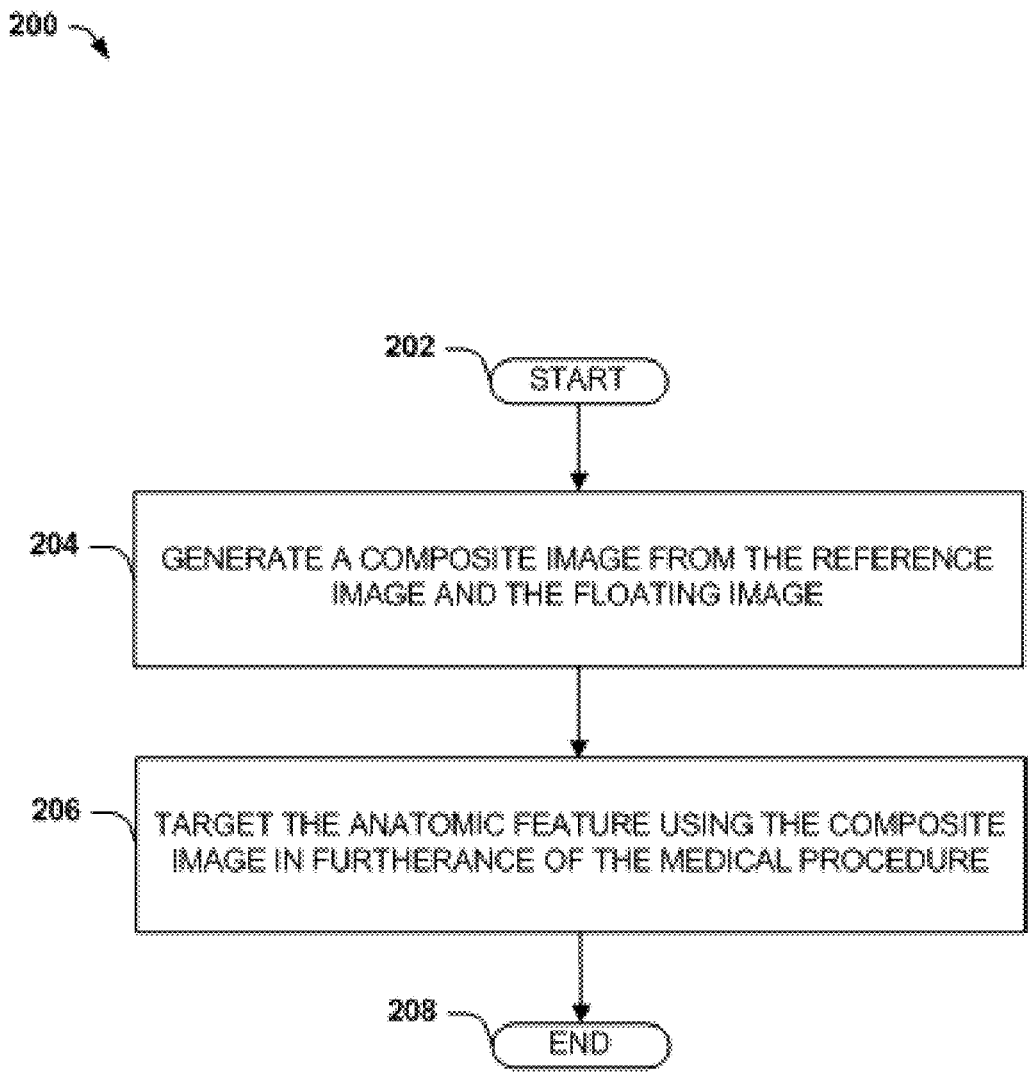
FIG. 11 is a flowchart illustration of a method of targeting an anatomic feature of an individual pertaining to a medical procedure illustrated in a reference image of the individual utilizing a first imaging modality and a floating image of the individual utilizing a floating imaging modality.

Accordingly, the techniques disclosed herein may be utilized in a method of targeting an anatomic feature of an individual pertaining to a medical procedure, wherein the anatomic feature is illustrated in a reference image of the individual that utilizes a reference imaging modality and a floating image of the individual that utilizes a floating imaging modality. An exemplary method 200 of this nature is illustrated in FIG. 11, wherein the exemplary method 200 begins at 202 and involves generating a composite image from the reference image and the floating image 204. The exemplary method 200 also involves targeting the anatomic feature using the composite image in furtherance of the medical procedure 206. Having achieved the targeting of the anatomic feature illustrated in the composite image, the method 200 ends at 208.

The composite image may also be generated by a system configured according to the techniques disclosed herein, such as the exemplary system of FIG. 6. The registration information produced by such a system may be processed by a composite image generating component that is configured to generate a composite image from the reference image voxel set and the transformed floating image voxel set. As disclosed herein, a system of this nature may be advantageously configured as a field-programmable gate array (FPGA) configured to represent at least one of the voxel enumerator unit, voxel coordinate transformation unit, the mutual histogram accumulator unit, the volumetric interpolator unit, and the mutual information calculator unit, such as in the exemplary system of FIG. 8. As the data presented in FIGS. 9A-9B demonstrates, a system having this configuration may be capable achieving high-performance computing that can generate a composite image according to these techniques in at least a near-realtime performance (e.g., within six minutes of capturing the images.)

System configured in this manner may therefore enable the generation of composite images that could not have otherwise been generated in a near-realtime performance in light of modern computing capabilities. Such near-realtime system performance, may be useful in time-sensitive scenarios, such as an operating room during the performance of a surgical procedure on the individual. Preoperative positron emission tomography (PET) imaging may be well-suited for this application, because PET imaging is often too time-consuming to generate intraoperatively, and therefore could not otherwise be used to provide near-realtime PET image about the anatomy of the individual. As a contrasting example, using the techniques provided herein, a healthcare provider (such as a surgical team) may generate an intraoperative image using an intraoperative imaging modality, generate a composite image from the preoperative PET image and the intraoperative image, and use the composite image to target an anatomic feature of the individual. One scenario for such targeting may involve a surgical probe, which may provide precise location information within the anatomy of the individual. A surgical probe of this nature may comprise, e.g., a positioning frame configured to triangulate the precise position and/or orientation of a surgical wand positioned therewithin. These techniques may therefore be adapted to include the surgical probe by detecting the position of the surgical probe within the surgical site, and displaying the position of the surgical probe coordinated with the composite image. Thus, a healthcare provider may be able to coordinate a position within the anatomy of the individual with a composite image based on a PET image, which heretofore may have been unachievable in a near-realtime performance. Many such uses may be devised by those in the ordinary skill in the art of imaging-based healthcare.

More generally, these techniques may facilitate the generation of composite images that are useful in many healthcare scenarios. For example, the composite image may be used to evaluating the presence, location, size, and/or condition of an anatomic feature in relation to the health state of the individual. For example, the composite image may be used to detect the presence, location, and qualities of a tumor or other abnormality, such as revealed in the composite image of FIG. 1C. As another example, the composite image may also be used to evaluate the condition of ordinary tissue and organs based on data generated via multiple modalities. This evaluation may reveal, e.g., information on the health state of a bone, as indicated both by the density of the bone illustrated in an X-ray image and by the metabolic activity of the associated tissue illustrated in a PET image. As a third example, the technique may be used during a surgical procedure to facilitate the targeting (e.g., identifying and localizing) of an anatomic feature such as a tumor. Many such uses may be devised by those of ordinary skill in the art of imaging-based healthcare.

Figure 12:
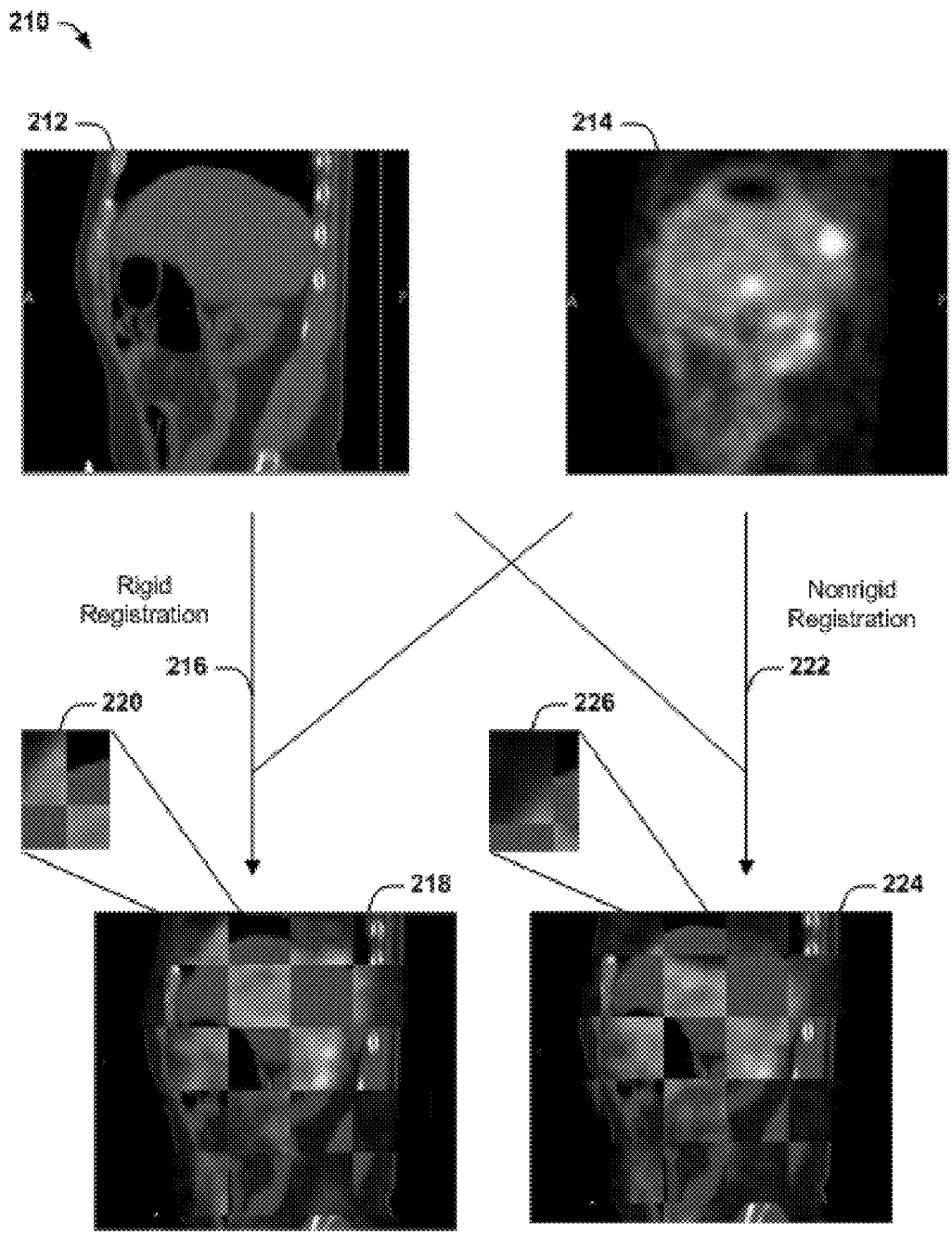
FIG. 12 is an illustration of a first exemplary contrasting registration of a positron emission tomography (PET) image with a computed tomography (CT) image according to a rigid registration technique and a nonrigid registration technique.

FIG. 12 presents a first contrasting example 210 involving the registration of two medical images (a preoperative PET image 212 with an intraoperative CT image 214) according to a rigid registration technique 216 vs. the nonrigid registration technique 222 presented herein. The use of each registration technique results in a registered intraoperative CT image, and each composite image is illustrated in FIG. 12 as a checkerboard pattern, where the comparatively darker sections illustrate portions of the preoperative PET image 212, and the comparatively lighter sections illustrate portions of the registered intraoperative CT image. For example, when the images are registered according to a rigid registration technique 216, the rigid registration composite image 218 reveals significant alignment errors between the preoperative PET image 212 and the registered intraoperative CT image. One such alignment error is illustrated in the exploded portion 220 near the top of the rigid registration composite image 218, which illustrates an inconsistent alignment of the organ surface between the preoperative PET image 212 and the registered intraoperative CT image. By contrast, when the images are registered according to the nonrigid registration technique 222, the nonrigid registered composite image 224 illustrates much better conformity of the organ surfaces in the preoperative PET image 212 as compared with the registered intraoperative CT image. This conformity is evident in the exploded portion 226 near the top of the nonrigid registration composite image 224, which reveals a smoother transition between the two images.

Figure 13:
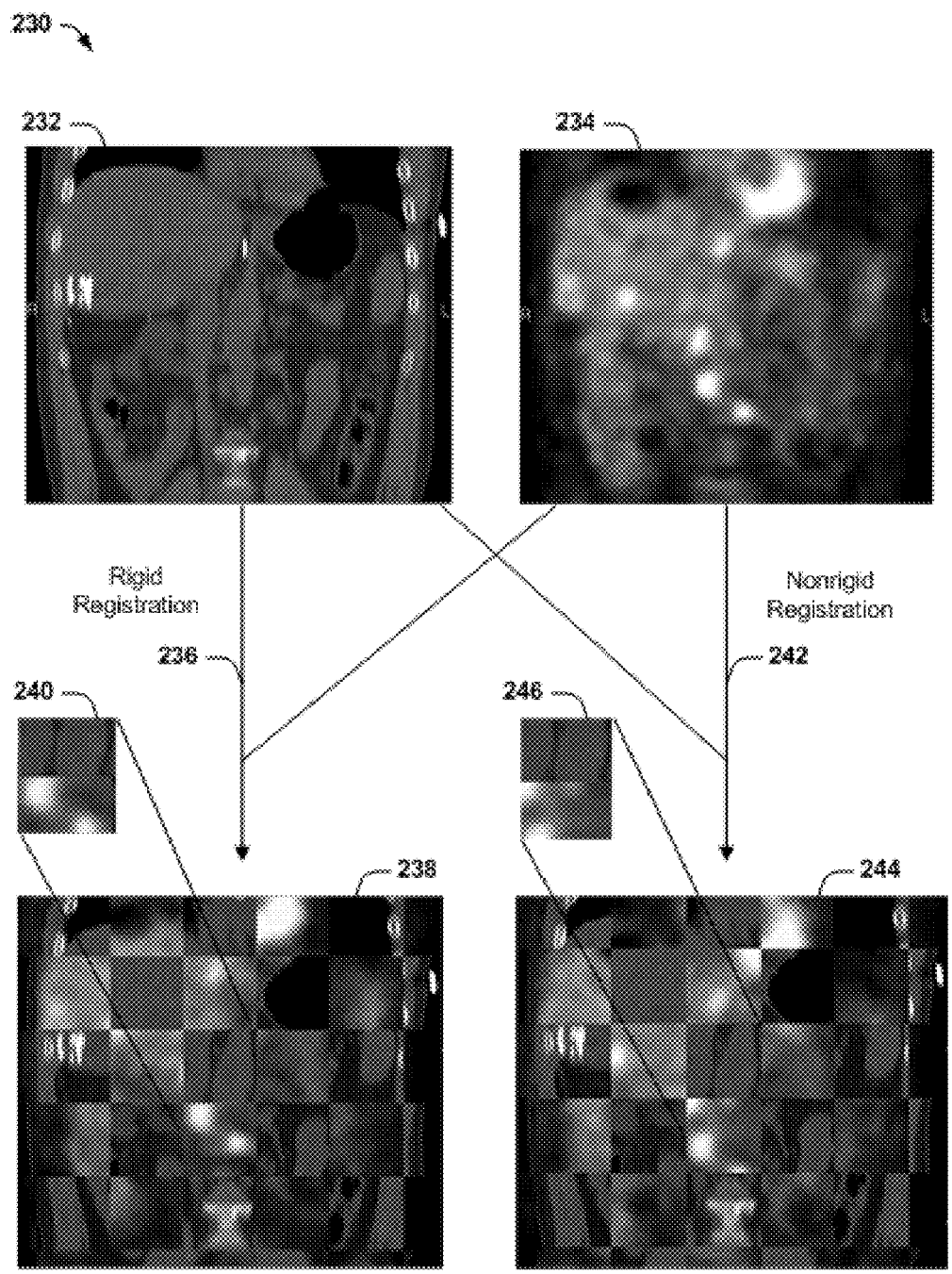
FIG. 13 is an illustration of a second exemplary contrasting registration of a computed tomography (CT) image with a positron emission tomography (PET) image according to a rigid registration technique and a nonrigid registration technique.

FIG. 13 presents a second contrasting example 230 involving the registration of two medical images (an intraoperative CT image 232 with a preoperative PET image 234) according to a rigid registration technique 236 vs. the nonrigid registration technique 242 presented herein. As in FIG. 12, each composite image generated by these registration techniques is illustrated as a checkerboard pattern, where the comparatively darker sections illustrate portions of the intraoperative CT image 232, and the comparatively lighter sections illustrate portions of the registered preoperative PET image. For example, when the images are registered according to a rigid registration technique 236, the rigid registration composite image 238 reveals significant alignment errors between the intraoperative CT image 232 and the registered preoperative PET image. One such alignment error is illustrated in the exploded portion 240 near the center of the rigid registration composite image 238, which illustrates a significant disparity between the tissue boundaries illustrated in the intraoperative CT image 232 (at top) and the registered preoperative PET image (at bottom.) By contrast, when the images are registered according to the nonrigid registration technique 242, the nonrigid registered composite image 244 illustrates much better continuation of tissue boundaries in the intraoperative CT image 232 as compared with the registered preoperative PET image. This continuation is evident in the exploded portion 246 near the center of the nonrigid registration composite image 244, which reveals a smoother continuation of tissue boundaries between the two images. It may be appreciated that the nonrigid registration technique 242 achieves significant improvement in the localization of areas of interest (such as the bright spot illustrated in the center of the preoperative PET image 234, which is correctly placed to the left of the tissue boundary illustrated in the exploded portion 246 of the nonrigid registered composite image 244, but is incorrectly displaced to the right in the exploded portion 240 of the rigid registered composite image 238.) Moreover, in contrast with a visual comparison of the intraoperative CT image 232 and the preoperative PET image 234, as well as the exploded portion 240 of the rigid registered composite image 238, the exploded portion 246 of the nonrigid registered composite image 244 provides more accurate information about the relative positioning of various features illustrated in each of the original images.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (assemblies, elements, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising." Also, "exemplary" as utilized herein merely means an example, rather than the best.

What is claimed is:

1. A system for registering a floating image with a reference image, the system comprising:

a reference image memory configured to store a reference image voxel set representing the reference image;

a floating image memory configured to store a floating image voxel set representing the floating image;

a voxel enumerator unit configured to count the voxels in sequential order along an axis of the reference image voxel set;

a voxel coordinate transformation unit configured to transform the voxels of the floating image voxel set with respect to the voxel in the reference image voxel set indicated by the voxel enumerator unit and to produce a transformed floating image voxel set;

a mutual histogram accumulator unit configured to accumulate a mutual histogram representing the transformed floating image voxel set interpolated with the reference image voxel set;

a volumetric interpolator unit configured to store in the mutual histogram accumulator unit the contribution to the mutual histogram of respective voxels of the transformed floating image voxel set interpolated with respective voxels of the reference image voxel set; and a mutual information calculator unit configured to calculate the mutual information between the reference image voxel set and the transformed floating image voxel set based on the mutual histogram.

2. The system of claim 1, wherein the floating image is obtained utilizing a preoperative PET imaging modality.

3. The system of claim 1, wherein the reference image is obtained utilizing one of a preoperative PET imaging modality, an X-ray imaging modality, an X-ray CT imaging modality, an ultrasound imaging modality, and an MRI imaging modality.

4. The system of claim 1, wherein the floating image memory configured comprises a configuration to store at least four copies of the floating image voxel set and to read a voxel octet from the floating image voxel set corresponding to a voxel in the reference image voxel set.

5. The system of claim 1, wherein the mutual information calculator unit comprises a configuration to calculate the mutual information based on the joint probabilities between the reference image voxel set and the transformed floating image voxel set as an aggregate of the individual probabilities of the reference image voxels with respective transformed floating image voxels.

6. The system of claim 5, wherein the configuration of the mutual information calculator unit further comprises a logarithmic lookup table, and the mutual information calculator unit is configured to consult the logarithmic lookup table to compute logarithmic components of the individual probabilities.

7. The system of claim 1, comprising an image registration control unit comprising a configuration to perform multi-pass registration of the floating image with the reference image until the mutual information between the reference image voxel set and the transformed floating image voxel set is within a desired mutual information range.

8. The system of claim 7, wherein the image registration control unit is configured, before initiating an at least second registration pass, to subdivide the voxels of the transformed floating image voxel set.

9. The system of claim 1, comprising a field-programmable gate array comprising a configuration to represent at least one of the voxel enumerator unit, voxel coordinate transformation unit, the mutual histogram accumulator unit, the volumetric interpolator unit, and the mutual information calculator unit.

10. A system for displaying a composite image from a floating image and a reference image, the system comprising:

a reference image memory configured to store a reference image voxel set representing the reference image;

a floating image memory configured to store a floating image voxel set representing the floating image;

a voxel enumerator unit configured to count the voxels in sequential order along an axis of the reference image voxel set;

a voxel coordinate transformation unit configured to transform the voxels of the floating image voxel set with respect to the voxel in the reference image voxel set indicated by the voxel enumerator unit and to produce a transformed floating image voxel set;

a mutual histogram accumulator unit configured to accumulate a mutual histogram representing the transformed floating image voxel set interpolated with the reference image voxel set;

a volumetric interpolator unit configured to store in the mutual histogram accumulator unit the contribution to the mutual histogram of respective voxels of the transformed floating image voxel set interpolated with respective voxels of the reference image voxel set;

a mutual information calculator unit configured to calculate the mutual information between the reference image voxel set and the transformed floating image voxel set based on the mutual histogram;

an image registration control unit configured to perform multi-pass registration of the floating image with the reference image until the mutual information between the reference image voxel set and the transformed floating image voxel set is within a desired mutual information range;

a composite image generating component configured to generate a composite image from the reference image voxel set and the transformed floating image voxel set; and a display unit configured to display the composite image.

11. The system of claim 10, the floating image utilizing a preoperative PET imaging modality.

12. The system of claim 10, the reference image utilizing at least one of a preoperative PET imaging modality, an X-ray imaging modality, an X-ray CT imaging modality, an ultrasound imaging modality, and an MRI imaging modality.

13. The system of claim 10, comprising an imaging unit configured to generate at least one of the reference image and the floating image.

14. The system of claim 10, comprising a field-programmable gate array configured to represent at least one of the voxel enumerator unit, voxel coordinate transformation unit, the mutual histogram accumulator unit, the volumetric interpolator unit, and the mutual information calculator unit.

* * * * *